United States Patent
Choi et al.

(10) Patent No.: US 11,690,721 B2
(45) Date of Patent: Jul. 4, 2023

(54) ARTIFICIAL JOINT

(71) Applicant: INDUSTRY-UNIVERSITY COOPERATION FOUNDATION HANYANG UNIVERSITY ERICA CAMPUS, Ansan-si (KR)

(72) Inventors: Youngjin Choi, Seongnam-si (KR); Geon Lee, Yongin-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 830 days.

(21) Appl. No.: 16/738,619

(22) Filed: Jan. 9, 2020

(65) Prior Publication Data

US 2020/0146829 A1 May 14, 2020

Related U.S. Application Data

(63) Continuation of application No. PCT/KR2018/007815, filed on Jul. 10, 2018.

(30) Foreign Application Priority Data

Jul. 10, 2017 (KR) .......... 10-2017-0087196
Feb. 1, 2018 (KR) .......... 10-2018-0012969

(51) Int. Cl.
*B25J 17/00* (2006.01)
*F16C 11/04* (2006.01)
(Continued)

(52) U.S. Cl.
CPC .......... *A61F 2/30* (2013.01); *A61F 2/54* (2013.01); *B25J 17/00* (2013.01); *F16C 11/045* (2013.01);
(Continued)

(58) Field of Classification Search
CPC .... B25J 17/02; B25J 17/0258; B25J 17/0283; F16C 11/00; F16C 11/04; F16B 7/00;
(Continued)

(56) References Cited

U.S. PATENT DOCUMENTS 3,263,800 A * 8/1966 Vissers .................. A01B 71/00
222/413
4,692,050 A * 9/1987 Kaufman ................ F16C 11/12
403/3
(Continued)

FOREIGN PATENT DOCUMENTS

EP 1234632 A1 * 8/2002 .......... B23Q 1/4852
FR 1469641 A * 2/1967
(Continued)

OTHER PUBLICATIONS

International Search Report for PCT/KR2018/007815 dated Oct. 29, 2018 [PCT/ISA/210].

*Primary Examiner* — Jonathan P Masinick
(74) *Attorney, Agent, or Firm* — Sughrue Mion, PLLC

(57) ABSTRACT

An artificial joint is provided. The artificial joint may comprise: a first joint member including a first bone replacement part, and a $(1\text{-}1)^{st}$ branch and a $(1\text{-}2)^{st}$ branch branched from opposite sides of the first bone replacement part; a second joint member including a second bone replacement part, and a $(2\text{-}1)^{nd}$ branch and a $(2\text{-}2)^{nd}$ branch branched from opposite sides of the second bone replacement part; a first main string connecting one side of the $(1\text{-}1)^{st}$ branch and one side of the $(2\text{-}1)^{nd}$ branch; a second main string connecting the one side of the $(1\text{-}1)^{st}$ branch and one side of the $(2\text{-}2)^{nd}$ branch; a third main string connecting one side of the $(1\text{-}2)^{st}$ branch and the one side of the $(2\text{-}1)^{nd}$ branch; and a fourth main string connecting the one side of the $(1\text{-}2)^{st}$ branch and the one side of the $(2\text{-}2)^{nd}$ branch.

22 Claims, 22 Drawing Sheets

(51) Int. Cl.
  *A61F 2/30* (2006.01)
  *A61F 2/54* (2006.01)
(52) U.S. Cl.
  CPC ............... *A61F 2002/30462* (2013.01); *A61F 2002/30546* (2013.01); *A61F 2002/30621* (2013.01); *Y10T 403/32041* (2015.01)
(58) Field of Classification Search
  CPC ........... Y10T 403/32; Y10T 403/32008; Y10T 403/32041; Y10T 403/32098; Y10T 403/32541; Y10T 403/32606; Y10T 403/32819; Y10T 403/32861
  See application file for complete search history.

(56) References Cited

U.S. PATENT DOCUMENTS

| | | | |
|---|---|---|---|
| 4,804,220 A * | 2/1989 | Rosheim | B25J 15/0009 403/114 |
| 4,878,393 A * | 11/1989 | Duta | B25J 17/0275 464/106 |
| 4,932,806 A | 6/1990 | Eklund et al. | |
| 5,765,443 A * | 6/1998 | Murase | B25J 17/0258 74/96 |
| 6,631,653 B2 * | 10/2003 | Brickner | G05G 9/04 403/57 |
| 7,048,768 B1 | 5/2006 | Rouse et al. | |
| 7,101,347 B2 | 9/2006 | Culhane et al. | |
| 7,140,969 B2 * | 11/2006 | Prucher | F16D 3/387 464/902 |
| 7,326,100 B2 * | 2/2008 | O'Brien | A63H 3/46 403/57 |
| 8,016,509 B2 * | 9/2011 | Gao | B25J 17/0275 464/56 |
| 8,708,593 B2 * | 4/2014 | Stratton | F16C 11/12 403/220 |
| 10,227,804 B2 * | 3/2019 | Howell | E05D 1/00 |
| 10,744,638 B2 * | 8/2020 | Kim | B25J 17/00 |
| 2009/0255364 A1 * | 10/2009 | Nishida | B25J 9/0051 74/490.07 |
| 2011/0130212 A1 * | 6/2011 | Sholev | F16D 3/18 464/150 |
| 2016/0051274 A1 * | 2/2016 | Howell | A61B 34/71 901/41 |
| 2022/0324122 A1 * | 10/2022 | Choi | B25J 17/0283 |

FOREIGN PATENT DOCUMENTS

| | | | | |
|---|---|---|---|---|
| GB | 2041879 A | * | 9/1980 | ............ B25J 13/02 |
| JP | 63-105896 A | | 5/1988 | |
| JP | 2006-015472 A | | 1/2006 | |
| KR | 10-0249419 B1 | | 12/1999 | |
| KR | 10-2012-0044200 A | | 5/2012 | |
| KR | 10-1328496 B1 | | 11/2013 | |
| WO | 99/32795 A1 | | 7/1999 | |

* cited by examiner

[Fig. 1]
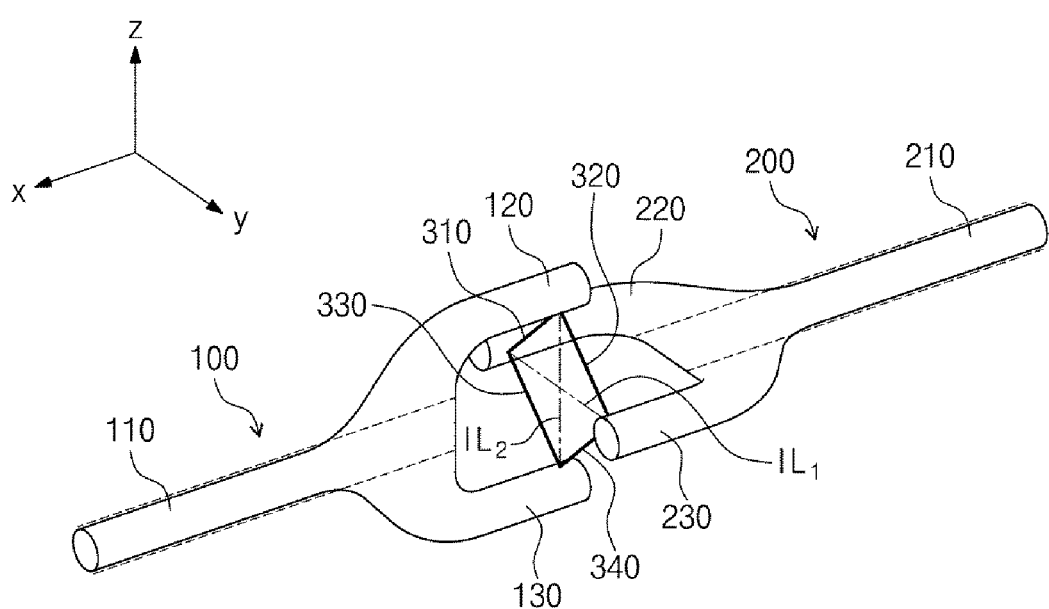

[Fig. 2]
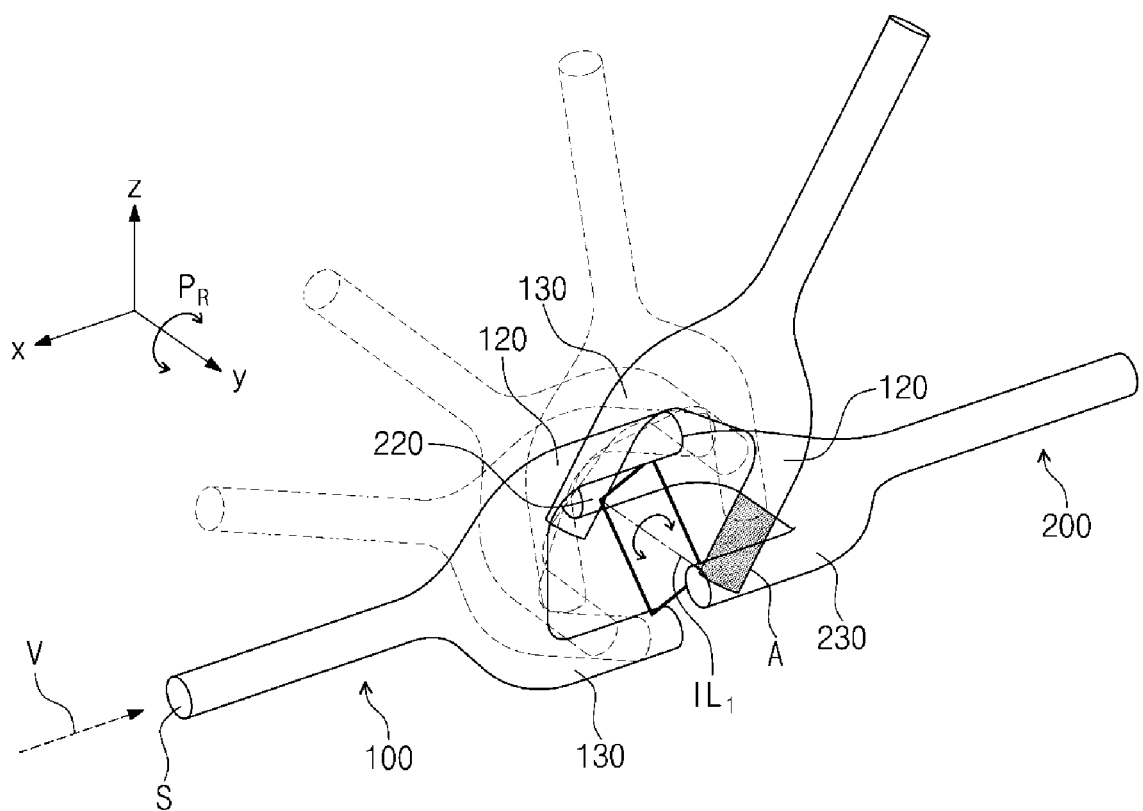

[Fig. 3]
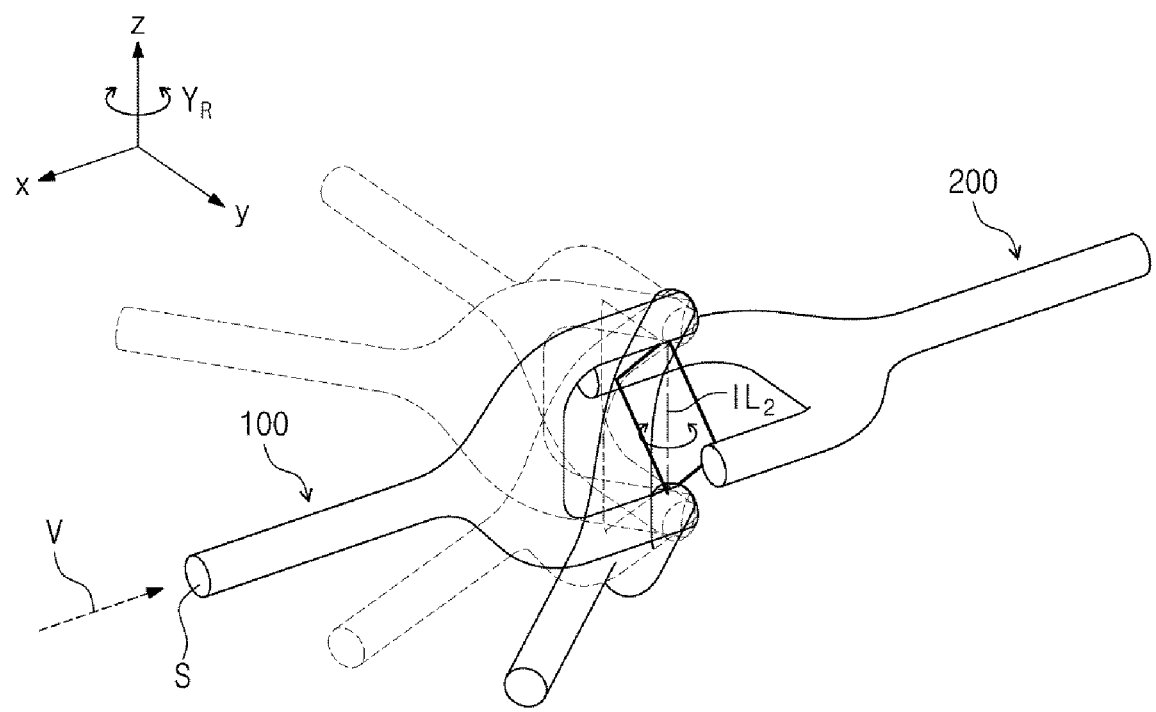

[Fig. 4]
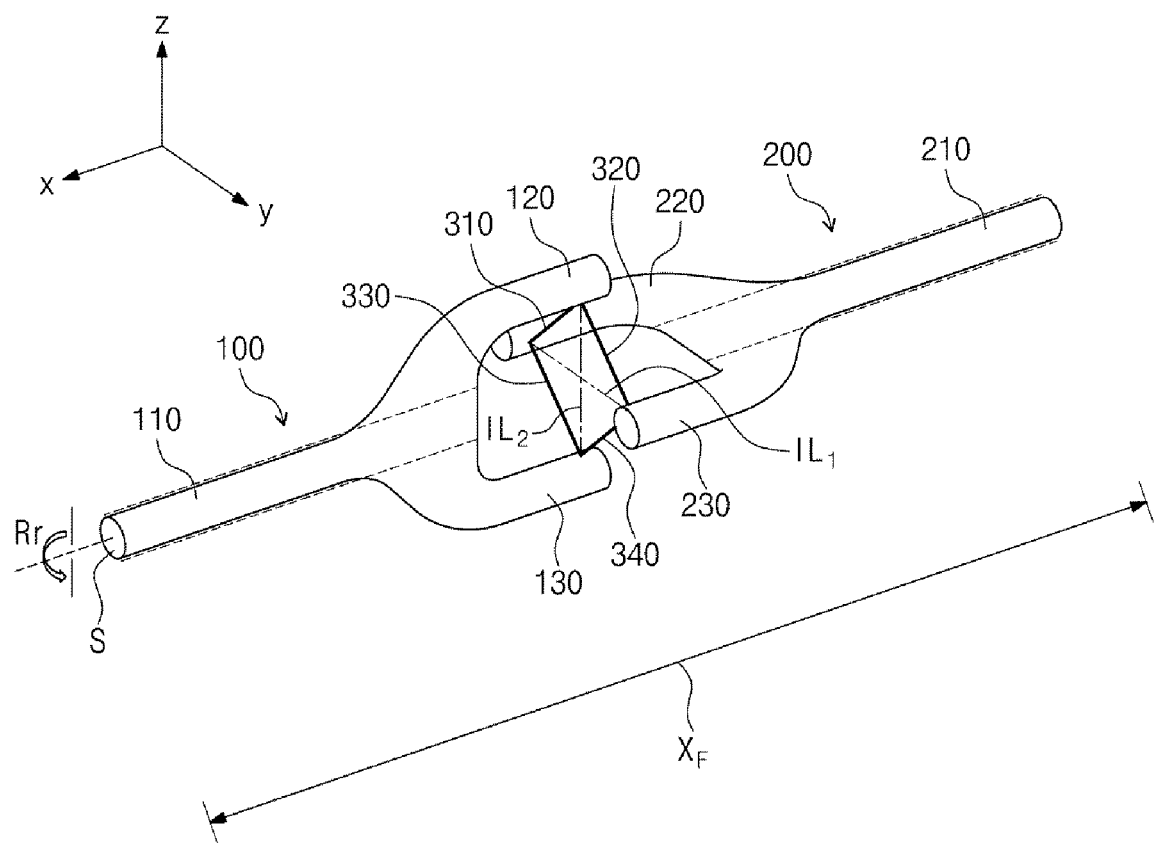

[Fig. 5]
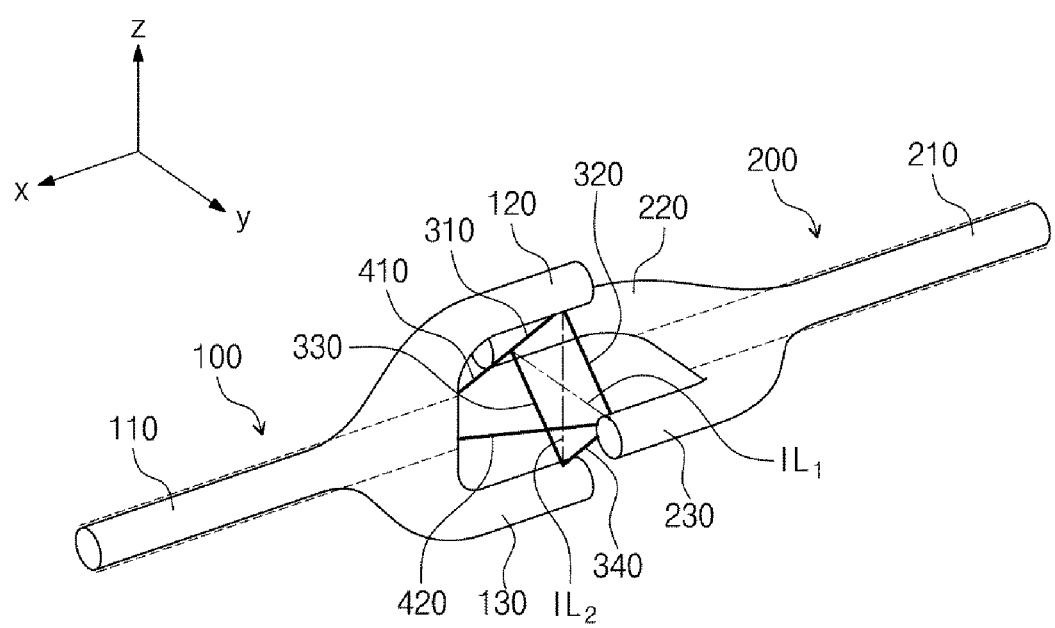

[Fig. 6]
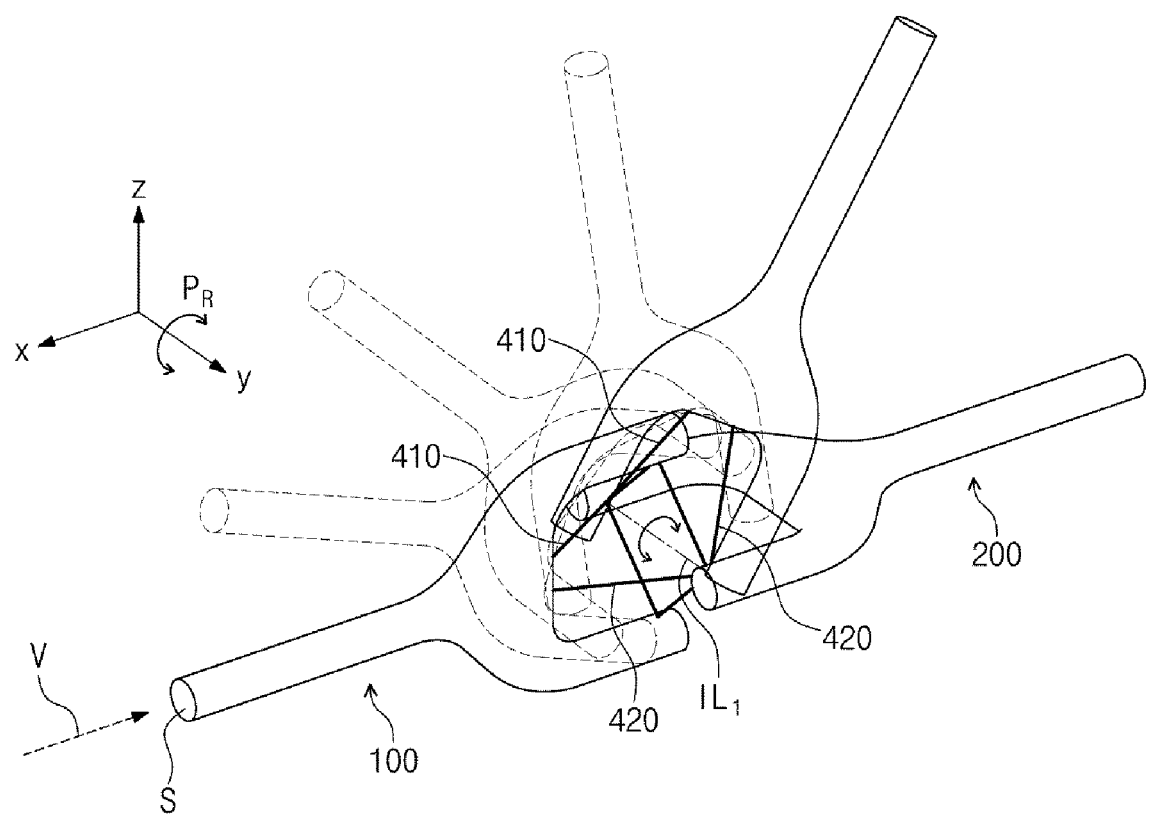

[Fig. 7]
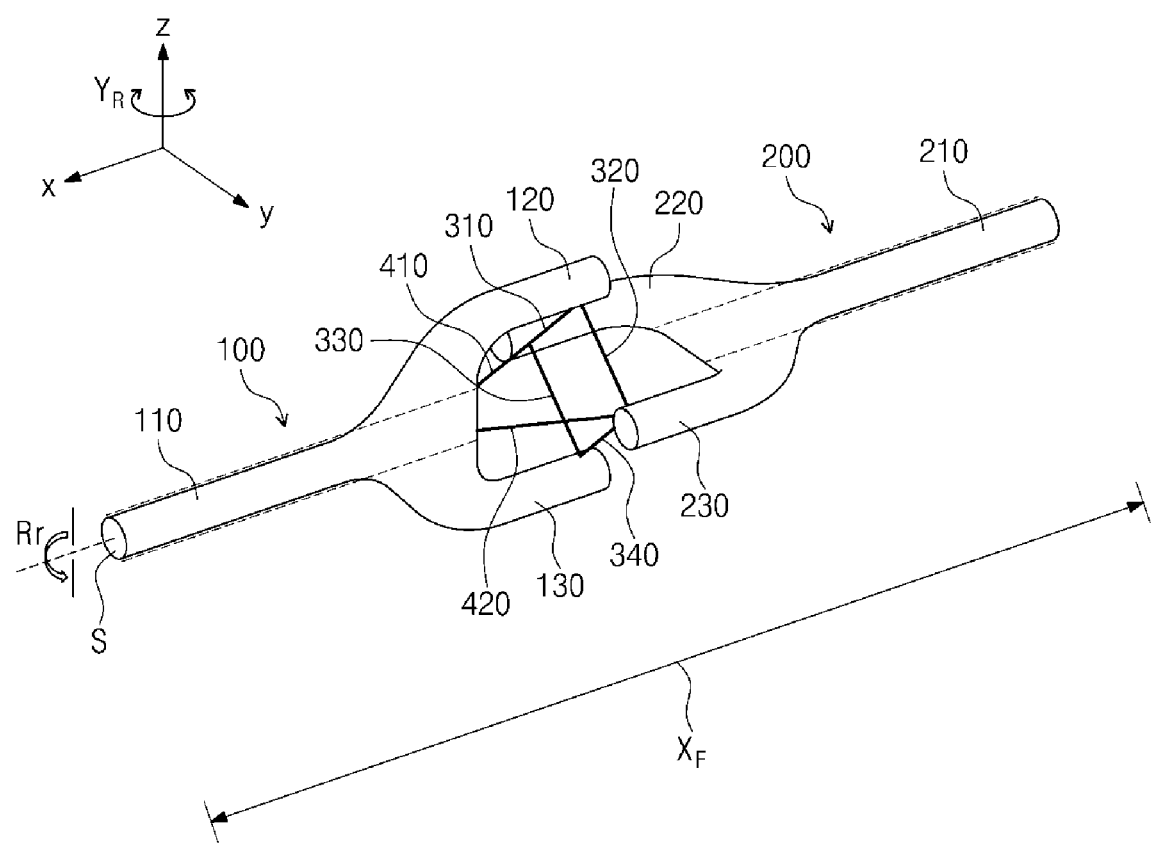

[Fig. 8]
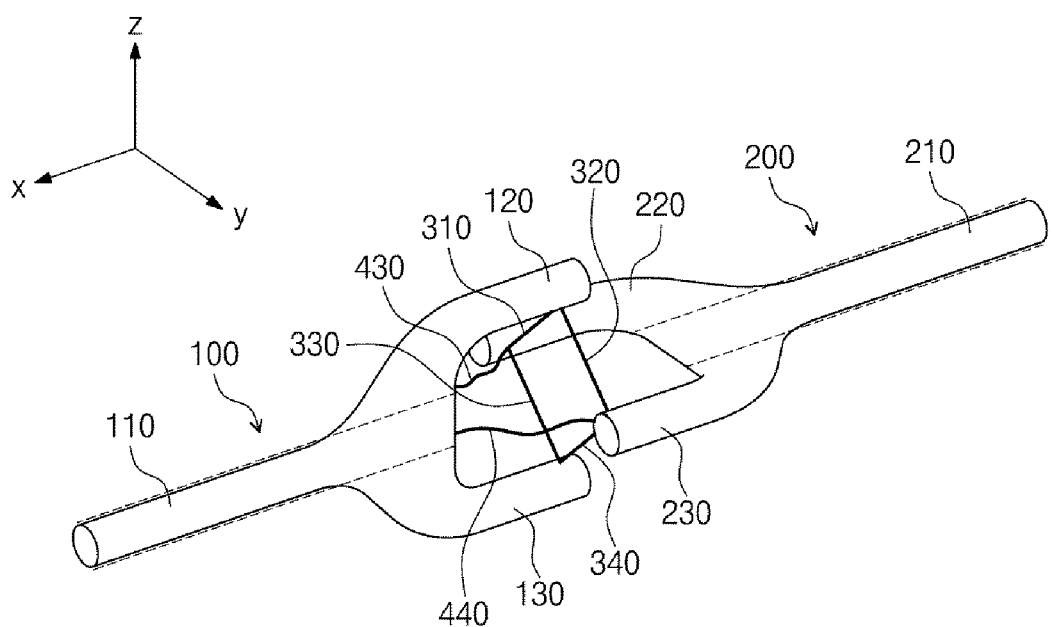

[Fig. 9]
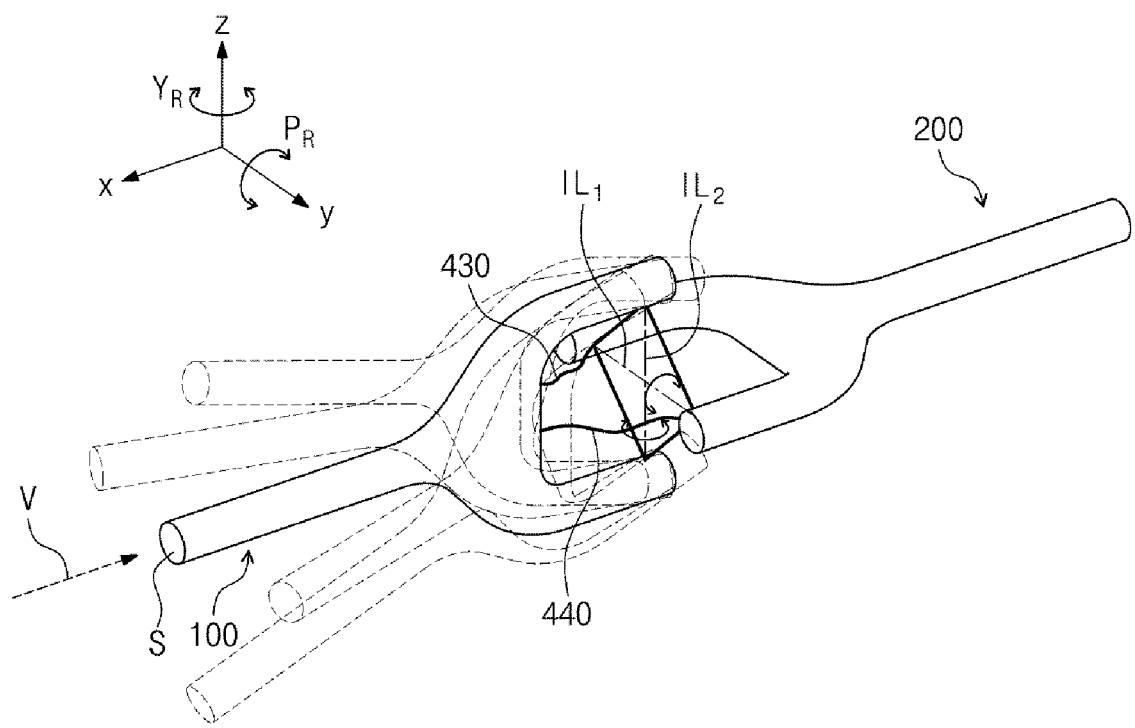

[Fig. 10]
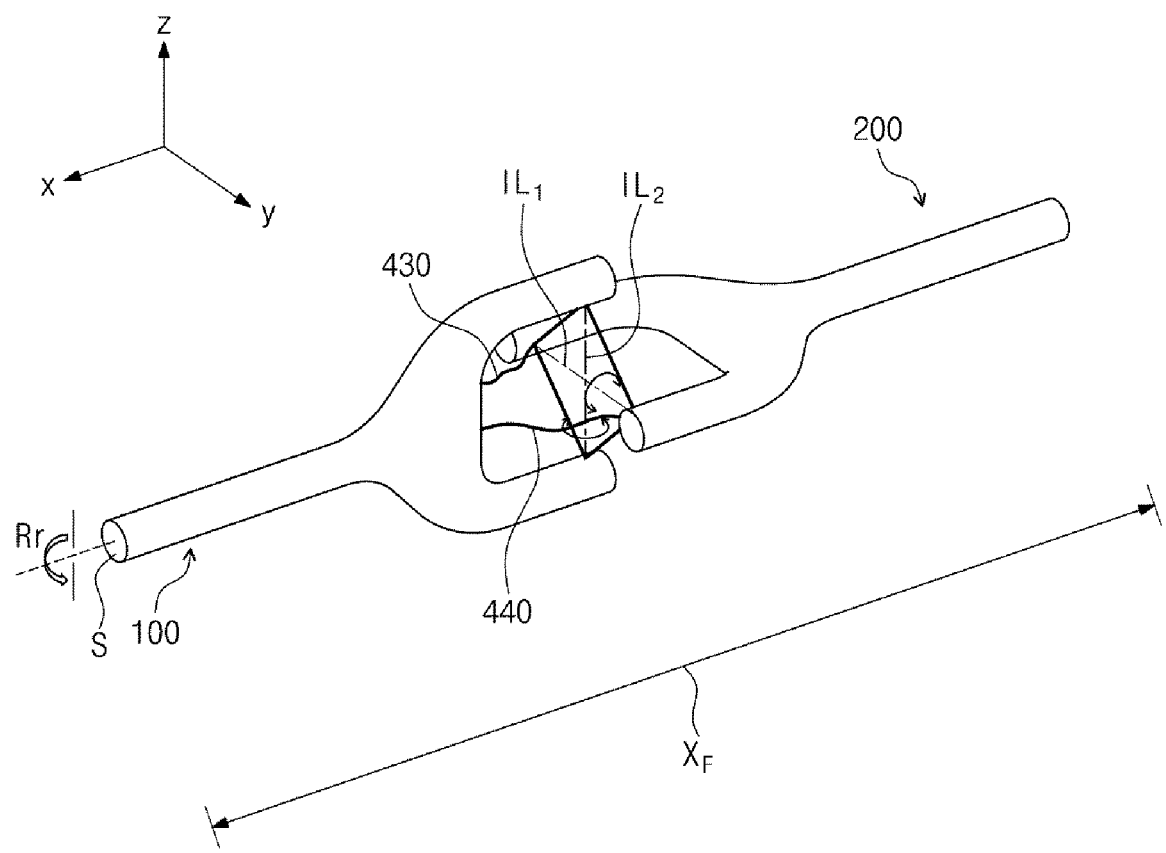

[Fig. 11]
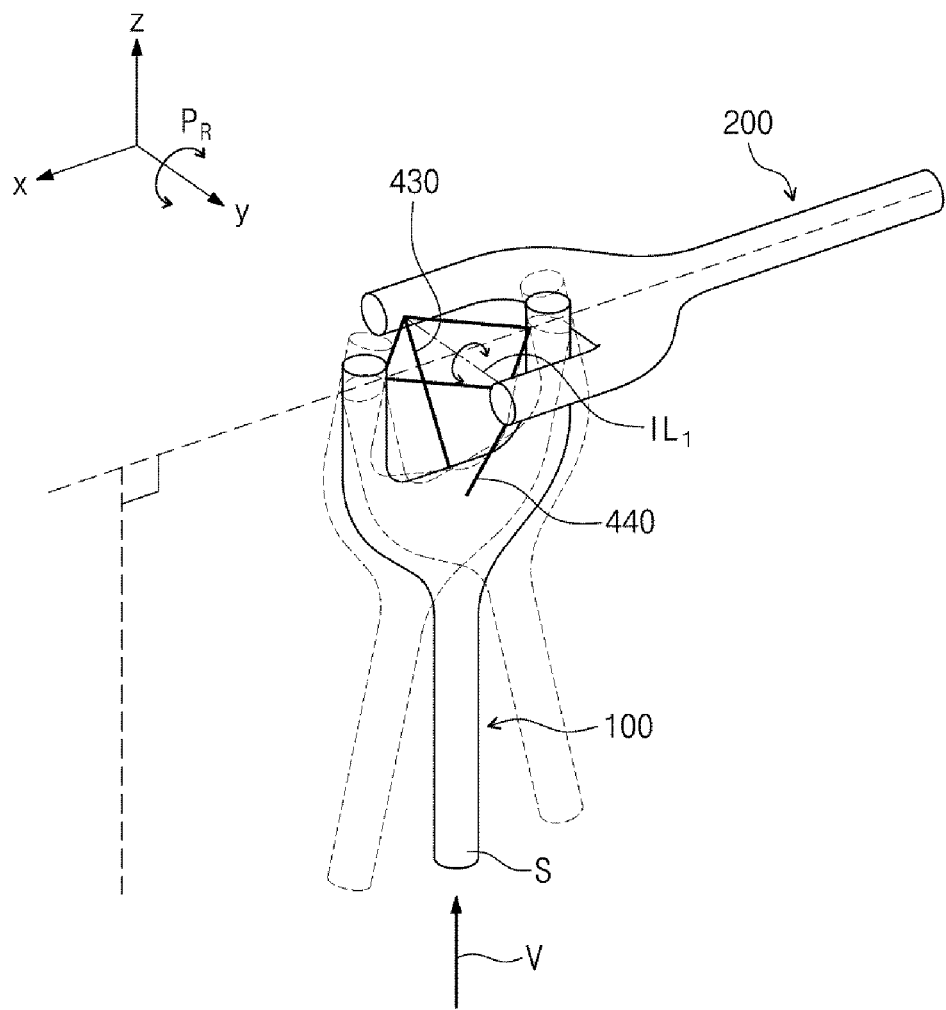

[Fig. 12]
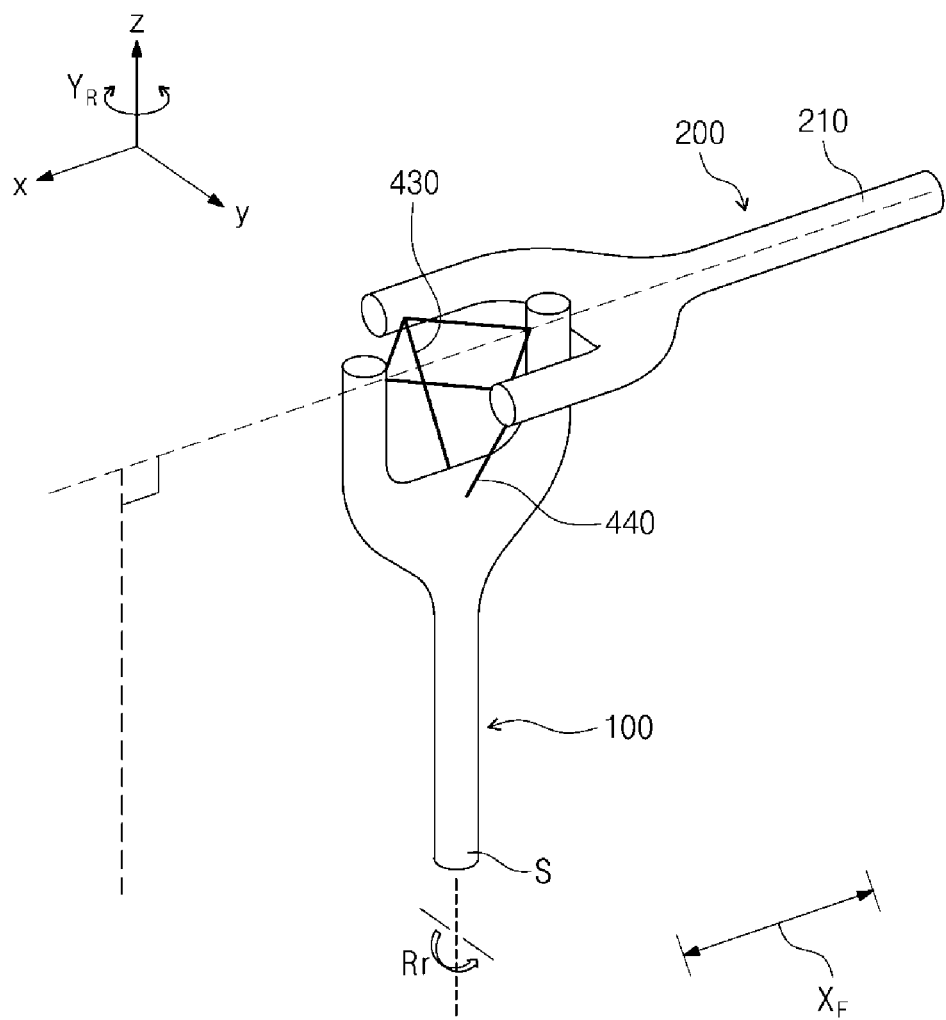

[Fig. 13]
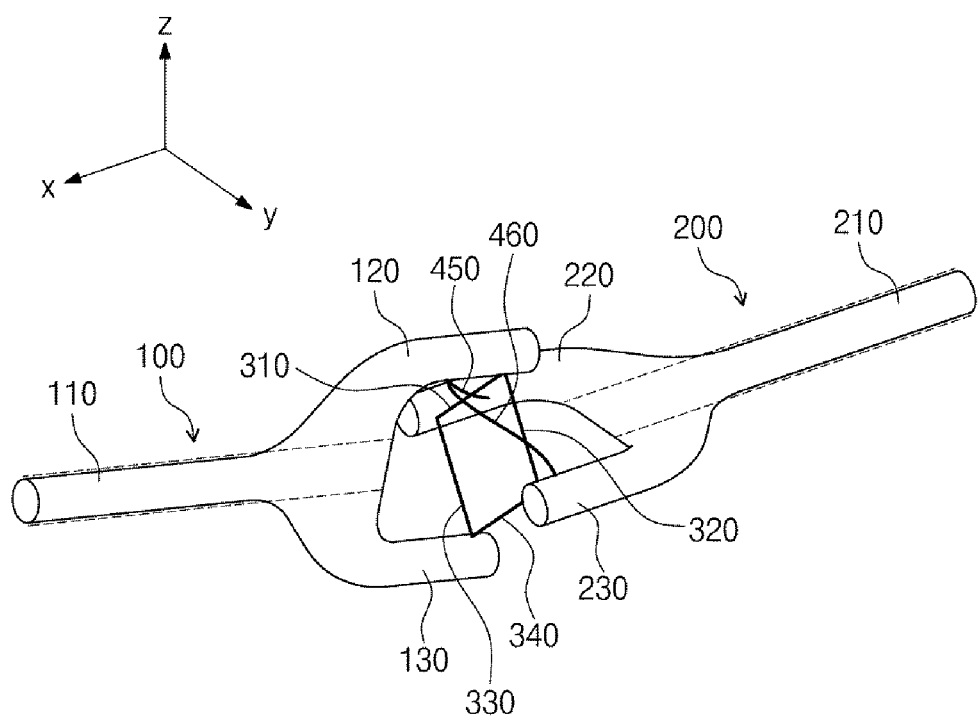

[Fig. 14]
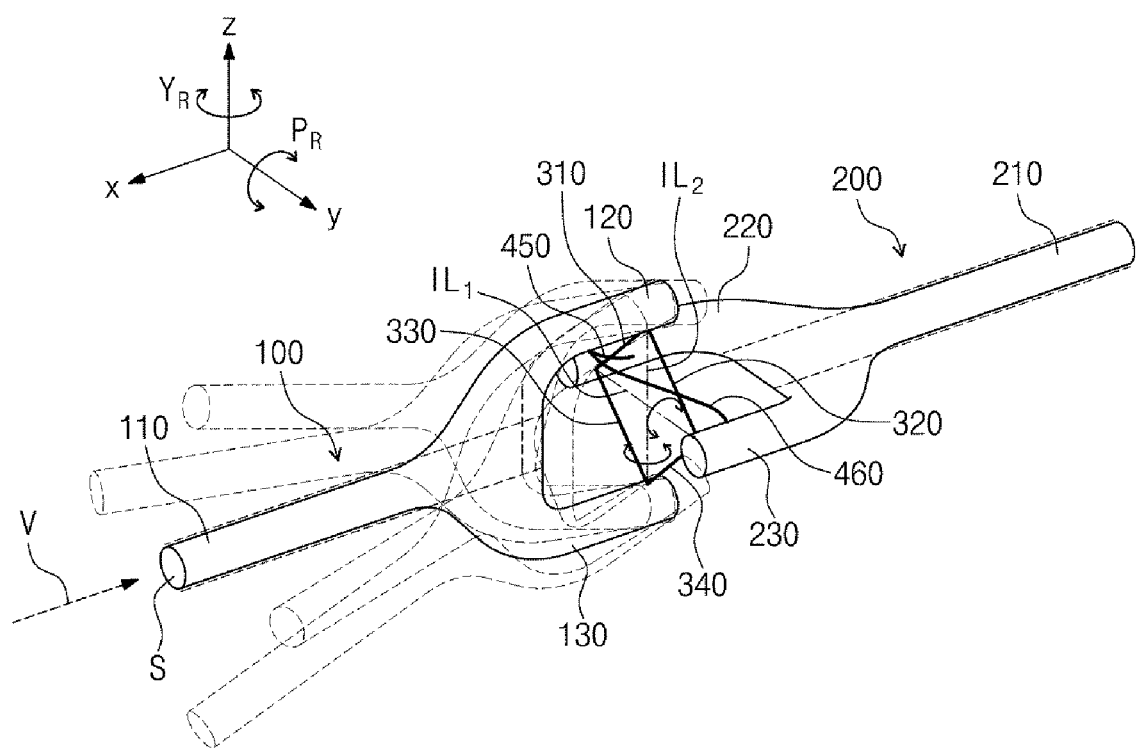

[Fig. 15]
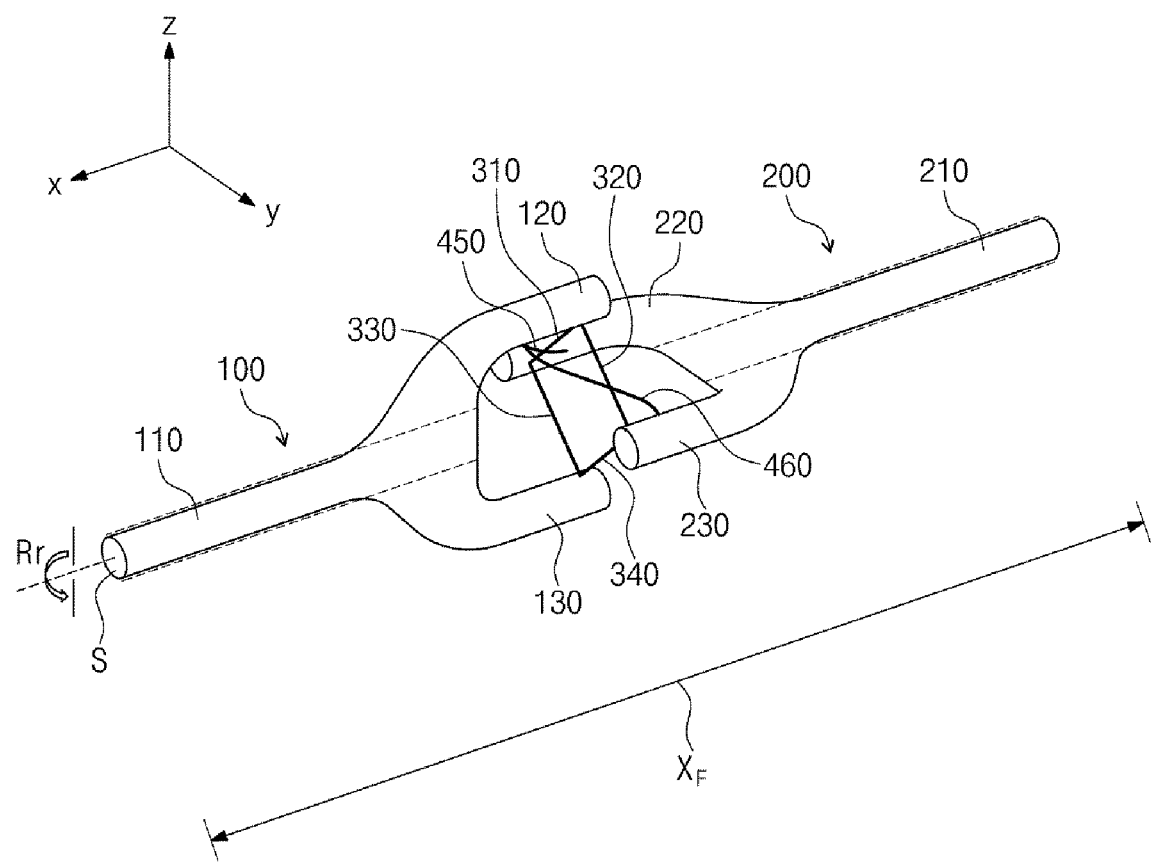

[Fig. 16]
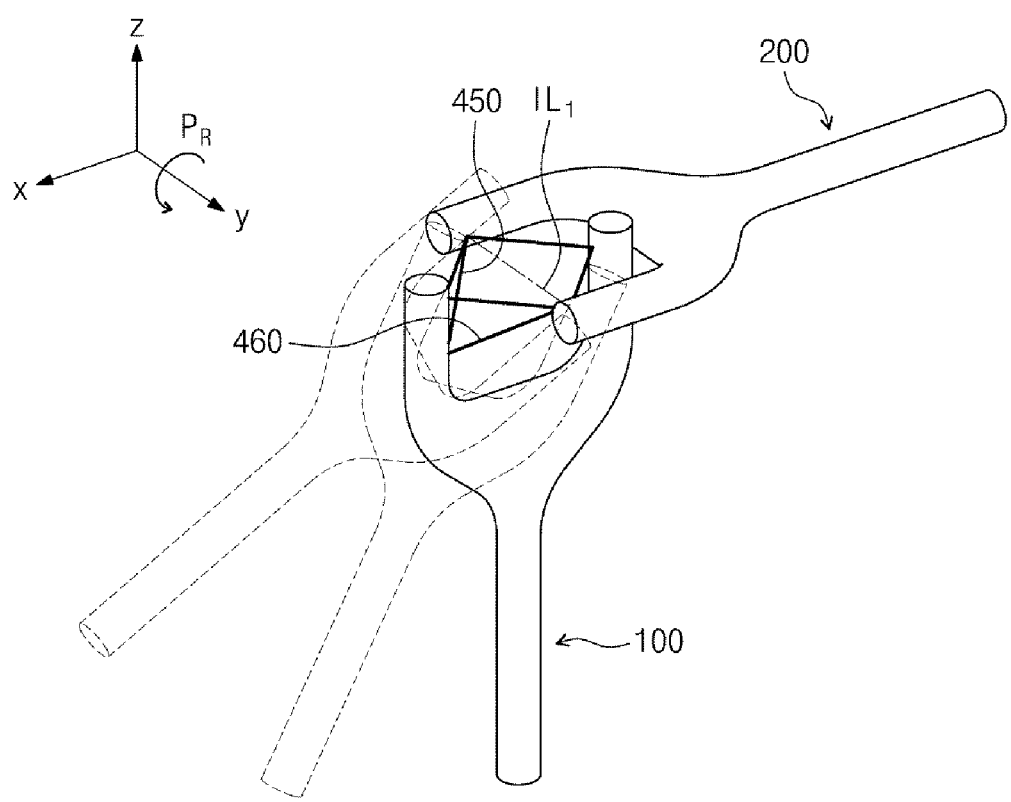

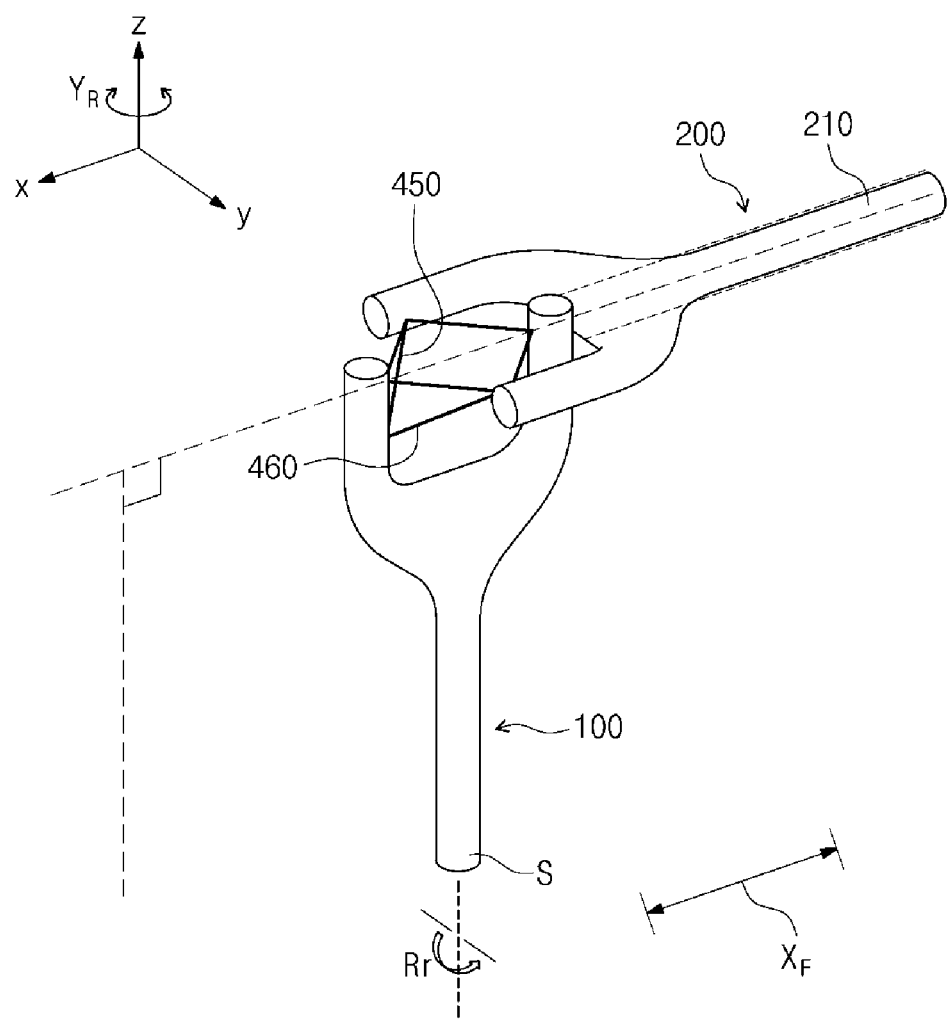
[Fig. 17]

[Fig. 18]
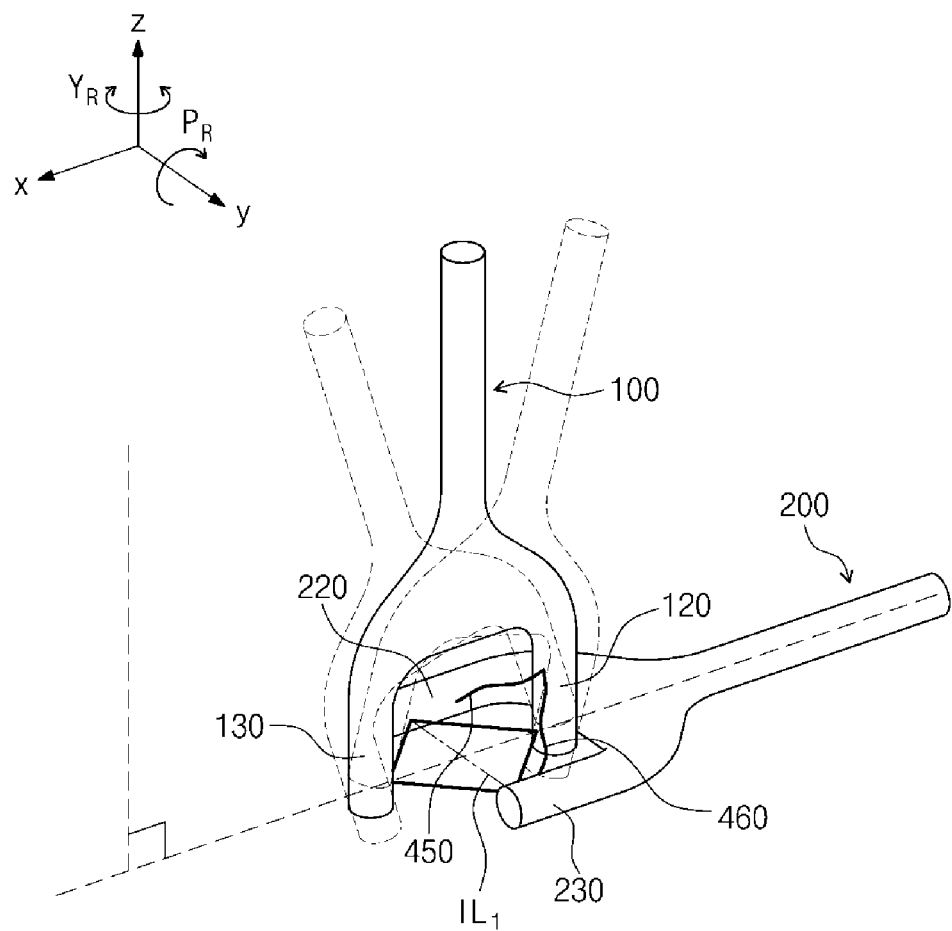

[Fig. 19]
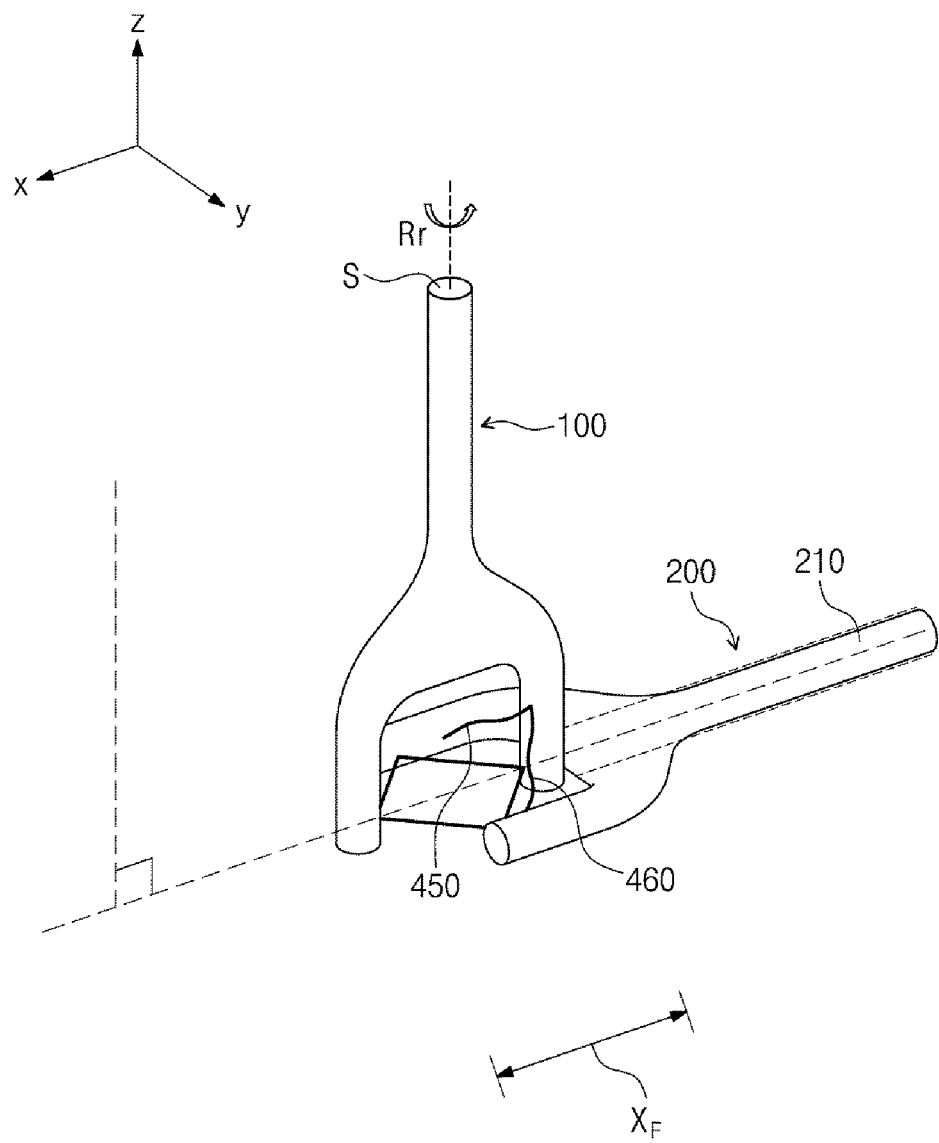

[Fig. 20]
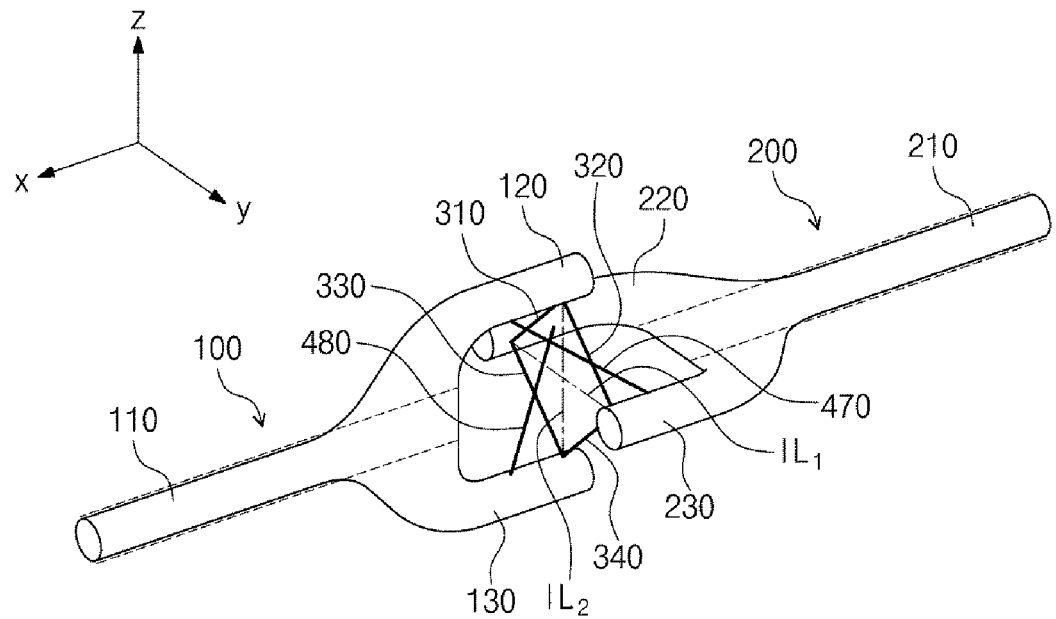
[Fig. 21]
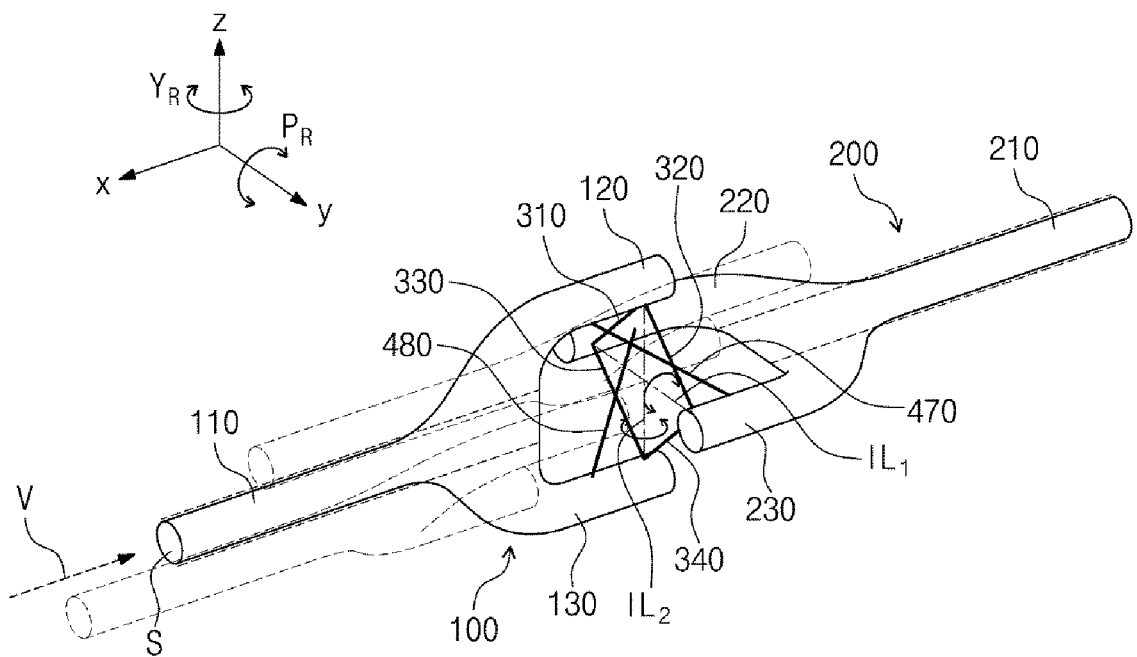

[Fig. 22]
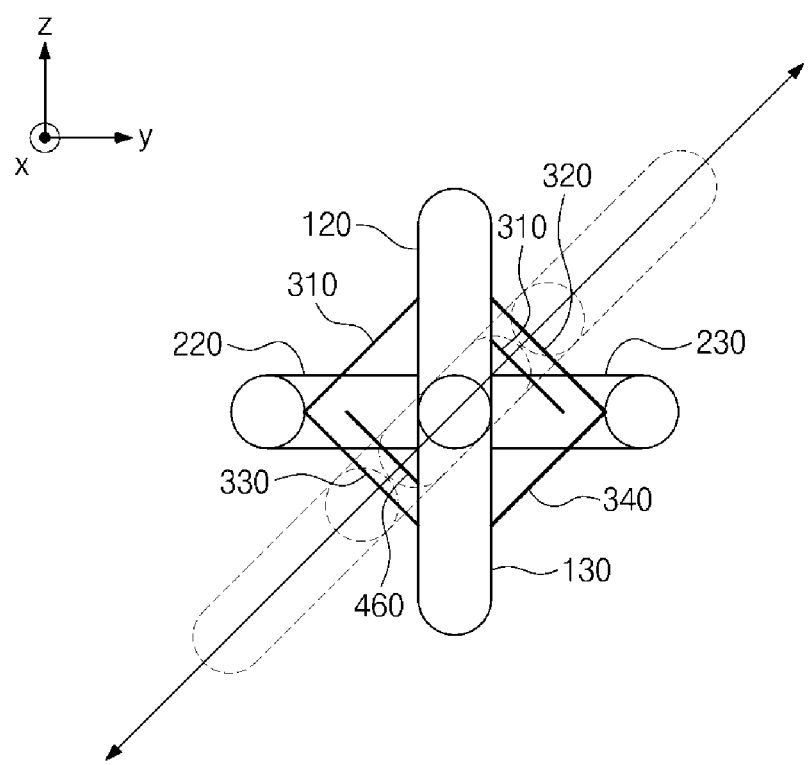

[Fig. 23]
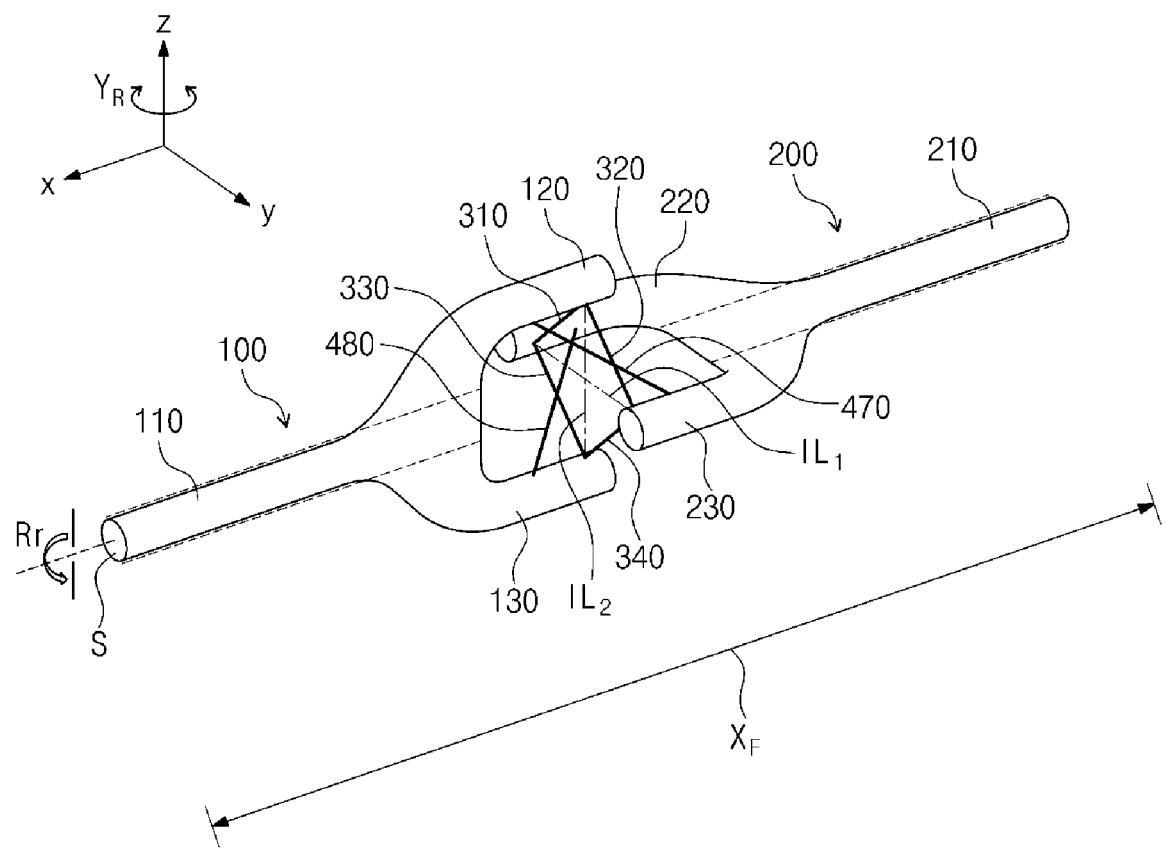

ARTIFICIAL JOINT

CROSS REFERENCE TO RELATED APPLICATIONS

This application is a Bypass application of International Application No. PCT/KR2018/007815, filed on Jul. 10, 2018, which claims priority from Korean Patent Application No. 10-2017-0087196, filed on Jul. 10, 2017, and Korean Patent Application No. 10-2018-0012969 filed on Feb. 1, 2018.

TECHNICAL FIELD

The present invention relates to an artificial joint, and relates to an artificial joint including a fixed joint member, a rotary joint member, and a string configured to connect the joint members.

BACKGROUND ART

Unlike industrial robots, service robots or rehabilitation robots come into contact with people in operations of the robots. Therefore, an impact that may be generated to the robot and a person due to such contact has to be considered. Most of existing robotic or mechanical joints have rigid bodies (links) tightly fixed to each other, and when an external impact is generated, most of the impact is transferred to a joint mechanism and a body subject to the impact. In addition, as the occasion demands, flexibility in a rotational direction may be applied through a control, while flexibility in a rotation axis direction may not be applied by a control technique alone. Furthermore, in the existing mechanical joints, a repulsive power acts between the rigid bodies (links) so that an abrasion phenomenon may occur due to friction, and such abrasion makes it difficult to use the mechanical joints for a long time. Accordingly, research and development have been continuously conducted on robot joints to solve the above problems.

DISCLOSURE

Technical Problem

One technical object of the present invention is to provide an artificial joint that simulates a flexible joint structure of a human body.

Another technical object of the present invention is to provide an artificial joint in which friction between members is reduced.

Still another technical object of the present invention is to provide an artificial joint with improved flexibility.

Yet another technical object of the present invention is to provide an artificial joint capable of generating various rotary joints.

The technical objects of the present invention are not limited to the above-described objects.

Technical Solution

In order to achieve the technical objects, the present invention provides an artificial joint.

In accordance with a first embodiment of the present invention, the artificial joint includes: a first joint member including a first bone frame, and a first-first branch and a first-second branch branched to both sides from the first bone frame; a second joint member including a second bone frame, and a second-first branch and a second-second branch branched to both sides from the second bone frame; a first main string configured to connect one side of the first-first branch to one side of the second-first branch; a second main string configured to connect the one side of the first-first branch to one side of the second-second branch; a third main string configured to connect one side of the first-second branch to the one side of the second-first branch; and a fourth main string configured to connect the one side of the first-second branch to the one side of the second-second branch.

According to the first embodiment, the first main string and the fourth main string may be parallel to each other, and the second main string and the third main string may be parallel to each other.

According to the first embodiment, the artificial joint may further include a sub-string, wherein the sub-string may provide a rotational characteristic between the first joint member and the second joint member.

According to the first embodiment, the first joint member may have two rotational degrees of freedom with respect to the second joint member.

According to the first embodiment, the first joint member may be able to perform pitch rotation with respect to the second joint member when viewing the second joint member in a longitudinal direction.

According to the first embodiment, the first joint member may be able to perform yaw rotation with respect to the second joint member when viewing the second joint member in a longitudinal direction.

According to the first embodiment, the artificial joint may have flexibility in at least one of a roll direction and a long-axis direction of the first bone frame and the second bone frame when viewing the second joint member in a longitudinal direction.

According to the first embodiment, a first virtual line configured to connect one end of the second-first branch to one end of the second-second branch and a second virtual line configured to connect one end of the first-first branch to one end of the first-second branch may cross each other.

According to the first embodiment, in the artificial joint where the first joint member rotates with respect to the second joint member in a pitch direction when viewing the second joint member in a longitudinal direction, the first-first branch or the first-second branch may pass through a virtual surface defined by a space between the second-first branch and the second-second branch.

According to a second embodiment, compared to the artificial joint according to the first embodiment described above, the artificial joint may further include: a first sub-string configured to connect one side of the first bone frame to the one side of the second-first branch; and a second sub-string configured to connect the one side of the first bone frame to the one side of the second-second branch.

According to the second embodiment, the first joint member may have one rotational degree of freedom with respect to the second joint member.

According to the second embodiment, the first joint member may be able to perform pitch rotation with respect to the second joint member when viewing the second joint member in a longitudinal direction.

According to the second embodiment, the artificial joint may have flexibility in at least one of a yaw direction, a roll direction, and a long-axis direction of the first bone frame and the second bone frame when viewing the second joint member in a longitudinal direction.

According to a third embodiment, compared to the artificial joint according to the first embodiment described above, the artificial joint may further include: a third sub-string configured to connect one side of the first bone frame to the one side of the second-first branch; and a fourth sub-string configured to connect the one side of the first bone frame to the one side of the second-second branch, wherein a tension of the third or fourth sub-string may be smaller than a tension of at least one of the first to fourth main strings.

According to a fourth embodiment, compared to the artificial joint according to the first embodiment described above, the artificial joint may further include: a fifth sub-string configured to connect the one side of the first-first branch to a middle portion of the second-first branch; and a sixth sub-string configured to connect the one side of the first-first branch to a middle portion of the second-second branch, wherein a tension of the fifth or sixth sub-string may be smaller than a tension of at least one of the first to fourth main strings.

According to the third or fourth embodiment, the artificial joint may have a different number of rotational degrees of freedom according to a pitch direction angle between the first joint member and the second joint member when viewing the second joint member in a longitudinal direction.

According to the third or fourth embodiment, the first joint member may have two degrees of freedom for pitch rotation and yaw rotation with respect to the second joint member when the pitch direction angle is smaller than a predetermined reference.

According to the third or fourth embodiment, the first joint member may have flexibility with respect to the second joint member in a yaw direction, a roll direction, and a long-axis direction of the first bone frame and the second bone frame.

According to the third or fourth embodiment, the first joint member may have one rotational degree of freedom for pitch rotation with respect to the second joint member when the pitch direction angle is larger than a predetermined reference.

According to the third or fourth embodiment, the first joint member may have flexibility with respect to the second joint member in a yaw direction, a roll direction, and a long-axis direction of the second bone frame when viewing the second joint member in the longitudinal direction.

According to the fourth embodiment, a rotational degree of freedom may be reduced in a case where the first joint member performs pitch rotation more than a predetermined reference with respect to the second joint member in a direction of the first-second branch when viewing the second joint member in a longitudinal direction.

According to a fifth embodiment, compared to the artificial joint according to the first embodiment described above, the artificial joint may further include: a seventh sub-string configured to connect a middle portion of the first-first branch to a middle portion of the second-second branch; and an eight sub-string configured to connect a middle portion of the first-second branch to a middle portion of the second-first branch, wherein the artificial joint may have a degree of freedom in pitch in a diagonal direction.

Advantageous Effects

According to an embodiment of the present invention, the artificial joint includes: a first joint member including a first bone frame, and a first-first branch and a first-second branch branched to both sides from the first bone frame; a second joint member including a second bone frame, and a second-first branch and a second-second branch branched to both sides from the second bone frame; a first main string configured to connect one side of the first-first branch to one side of the second-first branch; a second main string configured to connect the one side of the first-first branch to one side of the second-second branch; a third main string configured to connect one side of the first-second branch to the one side of the second-first branch; and a fourth main string configured to connect the one side of the first-second branch to the one side of the second-second branch. Accordingly, friction between members can be reduced so as to provide an artificial joint that can be used for a long time without abrasion.

In addition, according to the embodiment of the present invention, the artificial joint may further include: first and third sub-strings configured to connect one side of the first bone frame to the one side of the second-first branch; second and fourth sub-strings configured to connect the one side of the first bone frame to the one side of the second-second branch; a fifth sub-string configured to connect the one side of the first-first branch to a middle portion of the second-first branch; a sixth sub-string configured to connect the one side of the first-first branch to a middle portion of the second-second branch; a seventh sub-string configured to connect a middle portion of the first-first branch to a middle portion of the second-second branch; and an eight sub-string configured to connect a middle portion of the first-second branch to a middle portion of the second-first branch, wherein a tension of each of the third to sixth sub-strings may be smaller than a tension of at least one of the first to fourth main strings. Accordingly, an artificial joint capable of generating various rotary joints can be provided according to each embodiment.

DESCRIPTION OF DRAWINGS

FIG. 1 is a view showing an artificial joint according to a first embodiment of the present invention.

FIGS. 2 and 3 are views showing a movement of the artificial joint according to the first embodiment of the present invention.

FIG. 4 is a view showing flexibility of the artificial joint according to the first embodiment of the present invention.

FIG. 5 is a view showing an artificial joint according to a second embodiment of the present invention.

FIG. 6 is a view showing a movement of the artificial joint according to the second embodiment of the present invention.

FIG. 7 is a view showing flexibility of the artificial joint according to the second embodiment of the present invention.

FIG. 8 is a view showing an artificial joint according to a third embodiment of the present invention.

FIG. 9 is a view showing a movement of the artificial joint according to the third embodiment of the present invention when a pitch direction angle of the artificial joint is smaller than a reference.

FIG. 10 is a view showing flexibility of the artificial joint according to the third embodiment of the present invention when the pitch direction angle of the artificial joint is smaller than the reference.

FIG. 11 is a view showing a movement of the artificial joint according to the third embodiment of the present invention when the pitch direction angle of the artificial joint is larger than the reference.

FIG. 12 is a view showing flexibility of the artificial joint according to the third embodiment of the present invention when the pitch direction angle of the artificial joint is larger than the reference.

FIG. 13 is a view showing an artificial joint according to a fourth embodiment of the present invention.

FIG. 14 is a view showing a movement of the artificial joint according to the fourth embodiment of the present invention when a pitch direction angle of the artificial joint is smaller than a reference.

FIG. 15 is a view showing flexibility of the artificial joint according to the fourth embodiment of the present invention when the pitch direction angle of the artificial joint is smaller than the reference.

FIG. 16 is a view showing a movement of the artificial joint according to the fourth embodiment of the present invention when the pitch direction angle of the artificial joint is larger than the reference and a pitch direction is a counterclockwise direction.

FIG. 17 is a view showing flexibility of the artificial joint according to the fourth embodiment of the present invention when the pitch direction angle of the artificial joint is larger than the reference and the pitch direction is the counterclockwise direction.

FIG. 18 is a view showing a movement of the artificial joint according to the fourth embodiment of the present invention when the pitch direction angle of the artificial joint is larger than the reference and the pitch direction is a clockwise direction.

FIG. 19 is a view showing flexibility of the artificial joint according to the fourth embodiment of the present invention when the pitch direction angle of the artificial joint is larger than the reference and the pitch direction is the clockwise direction.

FIG. 20 is a view showing an artificial joint according to a fifth embodiment of the present invention.

FIG. 21 is a perspective view showing a movement of the artificial joint according to the fifth embodiment of the present invention.

FIG. 22 is a front view showing the movement of the artificial joint according to the fifth embodiment of the present invention.

FIG. 23 is a view showing flexibility of the artificial joint according to the fifth embodiment of the present invention.

MODE FOR INVENTION

Best Mode

Hereinafter, exemplary embodiments of the present invention will be described in detail with reference to the accompanying drawings. However, the technical idea of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the specification that one element is on another element, it means that a first element may be directly formed on a second element, or a third element may be interposed between the first element and the second element. Further, in the drawings, shapes and sizes are exaggerated for efficient description of the technical contents.

In the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments described and illustrated herein include their complementary embodiments. Further, the term "and/or" in the specification is used to include at least one of the elements enumerated before and after the term.

In the specification, the terms of a singular form may include plural forms unless the context clearly indicates otherwise. Further, the terms such as "including" and "having" are used to designate the presence of features, numbers, steps, elements, or combinations thereof described in the specification, and shall not be construed to preclude any possibility of presence or addition of one or more other features, numbers, steps, elements, or combinations thereof. Further, in the specification, the term "connection" may be used to include both indirectly and directly connecting a plurality of elements.

In addition, in the following description of the present invention, a detailed description of known functions and configurations incorporated herein will be omitted when it may make the subject matter of the present invention unnecessarily unclear.

Artificial Joint According to First Embodiment

FIG. 1 is a view showing an artificial joint according to a first embodiment of the present invention, FIGS. 2 and 3 are views showing a movement of the artificial joint according to the first embodiment of the present invention, and FIG. 4 is a view showing flexibility of the artificial joint according to the first embodiment of the present invention.

Referring to FIG. 1, the artificial joint according to the first embodiment may include a first joint member 100, a second joint member 200, and at least one of first to fourth main strings 310, 320, 330, and 340. Hereinafter, the description will be given for each component.

The first joint member 100 may include at least one of a first bone frame 110, a first-first branch 120, and a first-second branch 130. The first-first branch 120 and the first-second branch 130 may be branched to both sides from the first bone frame 110. In other words, the first joint member 100 may have a configuration in which the first-first branch 120 and the first-second branch 130 branch are branched to both sides with respect to the first bone frame 110. For example, the first-first branch 120 and the first-second branch 130 may be branched from one longitudinal end of the first bone frame 110. Accordingly, the first joint member 100 may have a Y-shape.

The second joint member 200 may include at least one of a second bone frame 210, a second-first branch 220, and a second-second branch 230. The second-first branch 220 and the second-second branch 230 may be branched to both sides from the second bone frame 210. In other words, the second joint member 220 may have a configuration in which the second-first branch 220 and the second-second branch 230 are branched to both sides with respect to the second bone frame 210. For example, the second-first branch 220 and the second-second branch 230 may be branched from one longitudinal end of the second bone frame 210. Accordingly, the second joint member 200 may have a Y-shape.

A first virtual line $IL_1$ configured to connect one end of the second-first branch 220 to one end of the second-second branch 230 and a second virtual line $IL_2$ configured to connect one end of the first-first branch 120 to one end of the first-second branch 130 may cross each other. Accordingly, the first joint member 100 and the second joint member 200 may face each other, such that a space between the first-first branch 120 and the first-second branch 130 and a space between the second-first branch 220 and the second-second branch 230 are arranged to cross each other. For example, the first virtual line $IL_1$ configured to connect the one end of the second-first branch 220 to the one end of the second-second branch 230 and the second virtual line $IL_2$ configured to connect the one end of the first-first branch 120 to the one end of the first-second branch 130 may cross each other at 90 degrees when viewed in an X-axis direction.

The first to fourth main strings 310, 320, 330, and 340 may connect the first and second joint members 100 and 200 to each other. In this case, the first main string 310 and the fourth main string 340 may be parallel to each other. In addition, the second main string 320 and the third main string 330 may be parallel to each other. As used herein, the term "parallel" may refer to a concept that includes "substantially parallel" as well as "theoretically parallel".

In detail, the first main string 310 may connect one side of the first-first branch 120 to one side of the second-first branch 220. The second main string 320 may connect the one side of the first-first branch 120 to one side of the second-second branch 230. The third main string 330 may connect one side of the first-second branch 130 to the one side of the second-first branch 220. The fourth main string 340 may connect the one side of the first-second branch 130 to the one side of the second-second branch 230.

Accordingly, one end of the first main string 310 and one end of the second main string 320 may be connected to the one side of the first-first branch 120. For example, the one end of the first main string 310 and the one end of the second main string 320 may be connected to the same node on the one side of the first-first branch 120. An opposite end of the first main string 310 and one end of the third main string may be connected to the one side of the second-first branch 220. For example, the opposite end of the first main string 310 and the one end of the third main string may be connected to the same node on the one side of the second-first branch 220. An opposite end of the third main string and one end of the fourth main string 340 may be connected to the one side of the first-second branch 130. For example, the opposite end of the third main string and the one end of the fourth main string 340 may be connected to the same node on the one side of the first-second branch 130. An opposite end of the fourth main string 340 and an opposite end of the second main string 320 may be connected to the one side of the second-second branch 230. For example, the opposite end of the fourth main string 340 and the opposite end of the second main string 320 may be connected to the same node on the one side of the second-second branch 230.

Accordingly, the first to fourth main strings 310, 320, 330, and 340 may form a parallelogram when viewed in the X-axis direction which is a longitudinal direction of the first and second joint members 100 and 200. As used herein, the term "parallelogram" may refer to a concept that includes a substantial parallelogram as well as a theoretical parallelogram.

In addition, the first to fourth main strings 310, 320, 330, and 340 may have the same tension. In this case, when no external force is applied to the first joint member 100 and the second joint member 200, as shown in FIG. 1, the first joint member 100 and the second joint member 200 may be parallel to each other in an initial state.

According to one embodiment, the first to fourth main strings 310, 320, 330, and 340 may be fixed by a wire sleeve (not shown). The wire sleeve (not shown) may be formed on an outer side of the first-first branch 120, the first-second branch 130, the second-first branch 220, and the second-second branch 230. In addition, the first-first branch 120, the first-second branch 130, the second-first branch 220, and the second-second branch 230 may have through-holes (not shown) at portions where the first to fourth main strings 310, 320, 330, and 340 are connected. Accordingly, the first to fourth main strings 310, 320, 330, and 340 may pass through the through-holes (not shown) and may be fixed by the wire sleeves (not shown).

According to one embodiment, the first to fourth main strings 310, 320, 330, and 340 may be formed of a material having elasticity. For example, the first to fourth main strings 310, 320, 330, and 340 may be formed of polyethylene (PE), nylon, or the like. Accordingly, the first to fourth main strings 310, 320, 330, and 340 may have flexibility in a long-axis direction. In addition, a degree of elasticity of the first to fourth main strings 310, 320, 330, and 340 may be adjusted. Accordingly, the artificial joint with adjustable flexibility, which will be described below, may be provided.

Referring to FIGS. 2 and 3, the first joint member 100 may have two rotational degrees of freedom with respect to the second joint member 200. In other words, relative rotation may be possible between the first joint member 100 and the second joint member 200 with the two rotational degrees of freedom. Hereinafter, for convenience of explanation, it is assumed that the first joint member 100 is a rotary joint member, and the second joint member 200 is a fixed joint member. On the contrary, the second joint member 200 may be the rotary joint member, and the first joint member 100 may be the fixed joint member. Hereinafter, the description will be given for each rotational degree of freedom.

Referring to FIG. 2, the first joint member 100 may be able to perform pitch rotation $P_R$ with respect to the second joint member 200 when viewing the first joint member 100 and/or the second joint member 200 in the longitudinal direction (X-axis direction). In other words, when viewing a section S from the view point of an observer V, the first joint member 100 may rotate with respect to the second joint member 200. When viewing from another point of view, the pitch rotation may represent that the first joint member 100 rotates about the first virtual line $IL_1$ in a clockwise or counterclockwise direction.

In the case where the first joint member 100 performs the pitch rotation $P_R$ with respect to the second joint member 200 when viewing the first joint member 100 and/or the second joint member 200 in the longitudinal direction (X-axis direction), the first-first branch 120 or the first-second branch 130 may pass through a virtual surface defined by the space between the second-first branch 220 and the second-second branch 230. For example, as shown as portion A in FIG. 2, when the first joint member 100 rotates about the first virtual line $IL_1$ in the counterclockwise direction, the first-first branch 120 may pass through the virtual surface defined by the space between the second-first branch 220 and the second-second branch 230. Due to geometric shapes of the first joint member 100 and the second joint member 200, a large rotation angle may be provided in a pitch direction.

Referring to FIG. 3, the first joint member 100 may be able to perform yaw rotation $Y_R$ with respect to the second joint member 200 when viewing the first joint member 100 and/or the second joint member 200 in the longitudinal direction (X-axis direction). In other words, when viewing the section S from the view point of the observer V, the first joint member 100 may rotate with respect to the second joint member 200. When viewing from another point of view, the yaw rotation may represent that the first joint member 100 rotates about the second virtual line $IL_2$ in the clockwise or counterclockwise direction.

In the case where the first joint member 100 performs the yaw rotation $Y_R$ with respect to the second joint member 200 when viewing in the longitudinal direction (X-axis direction) of the first joint member 100 and/or the second joint member 200, the second-first branch 220 or the second-second branch 230 may pass through a virtual surface defined by the space between the first-first branch 120 and the first-second branch 130. As described above, due to the geometric shapes of the first joint member 100 and the second joint member 200, a large rotation angle may be provided in a yaw direction.

Referring to FIG. 4, the artificial joint according to the first embodiment may have flexibility $X_F$ in at least one of a roll direction Rr and a long-axis direction (X-axis direction) of the first bone frame 110 and the second bone frame 210. According to one embodiment, the roll direction Rr may be a clockwise or counterclockwise direction when viewing in the longitudinal direction (X-axis direction) of the first joint member 100 and/or the second joint member 200.

In other words, the artificial joint according to the first embodiment may have flexibility with respect to a force pushing or pulling the first joint member 100 and the second joint member 200 in the longitudinal direction. In addition, the artificial joint according to the first embodiment may have flexibility with respect to a force pushing or pulling in a translational Z-axis direction and a translational Y-axis direction. Further, the artificial joint according to the first embodiment may have flexibility in the case of twisting the first joint member 100 and the second joint member 200.

Accordingly, the artificial joint according to the first embodiment of the present invention has been described. As described above, the artificial joint according to the first embodiment of the present invention may provide rotational degrees of freedom in the pitch direction and the yaw direction, and the artificial joint may have the flexibility in other directions due to flexibility of the main strings.

Hereinafter, artificial joints according to second to fifth embodiments, which further include a sub-string as compared with the artificial joint according to the first embodiment, will be described. The sub-string may generate a rotational trajectory to provide rotational characteristics to the artificial joint. In particular, unique rotation characteristics such as the number of degrees of freedom and the rotation trajectory may be provided according to the number of sub-strings, a connection position of the sub-string, and a tension of the sub-string.

First, the artificial joint according to the second embodiment including first and second sub-strings will be described with reference to FIGS. 5 to 7.

Artificial Joint According to Second Embodiment

FIG. 5 is a view showing an artificial joint according to a second embodiment of the present invention, FIG. 6 is a view showing a movement of the artificial joint according to the second embodiment of the present invention, and FIG. 7 is a view showing flexibility of the artificial joint according to the second embodiment of the present invention.

Referring to FIG. 5, compared to the artificial joint according to the first embodiment described with reference to FIG. 1, the artificial joint according to the second embodiment may further include at least one of first and second sub-strings 410 and 420. Accordingly, the detailed descriptions of the first joint member 100, the second joint member 200, and the first to fourth main strings 310, 320, 330, and 340 will be omitted.

According to one embodiment, the first sub-string 410 may connect one side of the first bone frame 110 to the one side of the second-first branch 220. In more detail, the first sub-string 410 may be connected to one end of the first bone frame 100. In addition, an opposite end of the first sub-string 410 may be connected to the same node as the first and third main strings 310 and 330. According to one embodiment, the second sub-string 420 may connect the one side of the first bone frame 110 to the one side of the second-second branch 220. In more detail, the second sub-string 420 may be connected to the one end of the first bone frame 100. In addition, an opposite end of the second sub-string 420 may be connected to the same node as the second and fourth main strings 320 and 340.

A tension of the first or second sub-string 410 or 420 may be the same as a tension of at least one of the first to fourth main strings 310, 320, 330, and 340. For example, the tension of the first or second sub-string 410 or 420 may be the same as the tension of each of the first to fourth main strings 310, 320, 330, and 340.

Referring to FIG. 6, unlike the artificial joint according to the first embodiment described with reference to FIG. 1, in the artificial joint according to the second embodiment, the first joint member 100 may have one rotational degree of freedom with respect to the second joint member 200. In detail, the first joint member 100 may perform the pitch rotation $P_R$ with respect to the second joint member 200 when viewing the first joint member 100 and/or the second joint member 200 in the longitudinal direction (X-axis direction).

In other words, compared to the artificial joint according to the first embodiment, the artificial joint according to the second embodiment further includes the first and second sub-strings 410 and 420, each having a tension which is the same as the tension of each of the first to fourth main strings 310, 320, 330, and 340, so that the yaw rotation $Y_R$ of the first joint member 100 with respect to the second joint member 200 may be limited, while the pitch rotation $P_R$ of the first joint member 100 with respect to the second joint member 200 may be performed.

Referring to FIG. 7, the artificial joint according to the second embodiment may have flexibility in at least one of the yaw direction $Y_R$, the roll direction Rr, and the long-axis direction $X_F$ of the first bone frame 110 and the second bone frame 210 when viewing the first joint member 100 and/or the second joint member 200 in the longitudinal direction (X-axis direction).

In other words, the artificial joint according to the second embodiment may have flexibility with respect to the force pushing or pulling the first joint member 100 and the second joint member 200 in the longitudinal direction. In addition, the artificial joint according to the second embodiment may have flexibility with respect to the force pushing or pulling in the translational Z-axis direction and the translational Y-axis direction. Further, the artificial joint according to the second embodiment may have flexibility in the case of pushing or pulling the first joint member 100 and the second joint member 200 in a y-axis direction shown in FIG. 7.

As described above, the artificial joint according to the second embodiment of the present invention may provide a rotational degree of freedom in the pitch direction, and the artificial joint may have the flexibility in other directions due to the flexibility of the main strings.

Accordingly, the artificial joint according to the second embodiment of the present invention has been described. Hereinafter, the artificial joints according to the third and fourth embodiments in which the number of rotational degrees of freedom varies according to an angle between the first joint member 100 and the second joint member 200 will be described with reference to FIGS. 8 to 19.

Artificial Joint According to Third Embodiment

FIG. 8 is a view showing an artificial joint according to a third embodiment of the present invention.

Referring to FIG. 8, compared to the artificial joint according to the first embodiment described with reference to FIG. 1, the artificial joint according to the third embodiment may further include at least one of third and fourth sub-strings 430 and 440. Accordingly, the detailed descriptions of the first joint member 100, the second joint member 200, and the first to fourth main strings 310, 320, 330, and 340 will be omitted.

According to one embodiment, the third sub-string 430 may connect one side of the first bone frame 110 to the one side of the second-first branch 220. In more detail, the third sub-string 430 may be connected to one end of the first bone frame 100. In addition, an opposite end of the third sub-string 430 may be connected to the same node as the first and third main strings 310 and 330. According to one embodiment, the fourth sub-string 440 may connect the one side of the first bone frame 110 to the one side of the second-second branch 220. In more detail, the fourth sub-string 440 may be connected to the one end of the first bone frame 100. In addition, an opposite end of the fourth sub-string 440 may be connected to the same node as the second and fourth main strings 320 and 340.

In other words, the third and fourth sub-strings 430 and 440 may be the same as the first and second sub-strings 410 and 420 described with reference to FIG. 5.

However, a tension of the third or fourth sub-string 430 or 440 may be smaller than the tension of at least one of the first to fourth main strings 310, 320, 330, and 340. For example, the tension of the third or fourth sub-string 430 or 440 may be smaller than the tension of each of the first to fourth main strings 310, 320, 330, and 340. Accordingly, the artificial joint according to the third embodiment may have a different number of rotational degrees of freedom according to an angle formed by the first joint member 100 and the second joint member 200.

FIG. 9 is a view showing a movement of the artificial joint according to the third embodiment of the present invention when a pitch direction angle of the artificial joint is smaller than a reference, and FIG. 10 is a view showing flexibility of the artificial joint according to the third embodiment of the present invention when the pitch direction angle of the artificial joint is smaller than the reference.

Referring to FIG. 9, the artificial joint according to the third embodiment may have two rotational degrees of freedom for the pitch rotation $P_R$ and the yaw rotation $Y_R$ when a pitch direction angle of the first joint member 100 with respect to the second joint member 200 is smaller than a predetermined reference. According to one embodiment, the pitch direction angle may refer to an angle formed by the first joint member 100 and the second joint member 200 when the first joint member 100 rotates about the first virtual line $IL_1$ in the clockwise or counterclockwise direction.

In other words, since the tension of the third or fourth sub-string 430 or 440 is smaller than the tension of each of the first to fourth main strings 310, 320, 330, and 340, that is, since the third and fourth sub-strings 430 and 440 are loose, the artificial joint according to the third embodiment may have degrees of freedom for the yaw rotation $Y_R$ as well as the pitch rotation $P_R$ unlike the artificial joint according to the second embodiment described with reference to FIG. 6.

Referring to FIG. 10, the artificial joint according to the third embodiment may have flexibility $X_F$ in the roll direction Rr and the long-axis direction of the first bone frame and the second bone frame when the pitch direction angle of the first joint member 100 with respect to the second joint member 200 is smaller than the predetermined reference. In addition, the artificial joint according to the third embodiment may have flexibility with respect to the force pushing or pulling in the translational Z-axis direction and the translational Y-axis direction.

In other words, the artificial joint according to the third embodiment may have flexibility in the case of pulling, pushing, and twisting the first joint member 100 and the second joint member 200 when the pitch direction angle of the first joint member 100 with respect to the second joint member 200 is smaller than the predetermined reference.

FIG. 11 is a view showing a movement of the artificial joint according to the third embodiment of the present invention when the pitch direction angle of the artificial joint is larger than the reference, and FIG. 12 is a view showing flexibility of the artificial joint according to the third embodiment of the present invention when the pitch direction angle of the artificial joint is larger than the reference.

Referring to FIG. 11, the artificial joint according to the third embodiment may have one rotational degree of freedom for the pitch rotation $P_R$ when the pitch direction angle of the first joint member 100 with respect to the second joint member 200 is larger than the predetermined reference. For example, when the pitch direction angle of the first joint member 100 with respect to the second joint member 200 is 90 degrees, the first joint member 100 may have one rotational degree of freedom for the pitch rotation $P_R$.

In detail, as the pitch direction angle of the first joint member 100 with respect to the second joint member 200 increases, the tensions of the third and fourth sub-strings 430 and 440 may be increased. As the tensions of the third and fourth sub-strings 430 and 440 increases, in the artificial joint according to the third embodiment, the yaw rotation $Y_R$ of the first joint member 100 with respect to the second joint member 200 may be limited, while the pitch rotation $P_R$ of the first joint member 100 with respect to the second joint member 200 may be performed.

Referring to FIG. 12, when the pitch direction angle of the first joint member 100 with respect to the second joint member 200 is larger than the predetermined reference, the artificial joint according to the third embodiment may have the flexibility $X_F$ in the yaw direction $Y_R$, the roll direction Rr, and the long-axis direction of the second bone frame 210 based on the longitudinal direction of the first joint member 100 (z-axis direction in FIG. 12). In addition, the artificial joint according to the third embodiment may have flexibility with respect to the force pushing or pulling in the translational Z-axis direction and the translational Y-axis direction.

As described above, the artificial joint according to the third embodiment of the present invention may provide the rotational degrees of freedom in the pitch direction and the yaw direction when the pitch direction angle is smaller than the reference, and the artificial joint may have the flexibility in other directions due to the flexibility of the main strings. In addition, the artificial joint according to the third embodiment of the present invention may provide the rotational degree of freedom in the pitch direction when the pitch direction angle is larger than the reference, and the artificial joint may have the flexibility in other directions due to the flexibility of the main strings.

Artificial Joint According to Fourth Embodiment

FIG. 13 is a view showing an artificial joint according to a fourth embodiment of the present invention.

Referring to FIG. 13, compared to the artificial joint according to the first embodiment described with reference to FIG. 1, the artificial joint according to the fourth embodiment may further include at least one of fifth and sixth sub-strings 450 and 460. Accordingly, the detailed descriptions of the first joint member 100, the second joint member 200, and the first to fourth main strings 310, 320, 330, and 340 will be omitted.

According to one embodiment, the fifth sub-string 450 may connect the one side of the first-first branch 120, for example, a middle portion of the first-first branch 120 to a middle portion of the second-first branch 220. According to one embodiment, the sixth sub-string 460 may connect the one side of the first-first branch 120, for example, the middle portion of the first-first branch 120 to a middle portion of the second-second branch 230.

In this case, a tension of the fifth or sixth sub-string 450 or 460 may be smaller than the tension of at least one of the first to fourth main strings 310, 320, 330, and 340. For example, the tension of the fifth or sixth sub-string 450 or 460 may be smaller than the tension of each of the first to fourth main strings 310, 320, 330, and 340. Accordingly, the artificial joint according to the fourth embodiment may have a different number of rotational degrees of freedom according to the angle formed by the first joint member 100 and the second joint member 200.

FIG. 14 is a view showing a movement of the artificial joint according to the fourth embodiment of the present invention when a pitch direction angle of the artificial joint is smaller than a reference, and FIG. 15 is a view showing flexibility of the artificial joint according to the fourth embodiment of the present invention when the pitch direction angle of the artificial joint is smaller than the reference.

Referring to FIG. 14, the artificial joint according to the fourth embodiment may have two rotational degrees of freedom for the pitch rotation $P_R$ and the yaw rotation $Y_R$ when a pitch direction angle of the first joint member 100 with respect to the second joint member 200 is smaller than the predetermined reference. According to one embodiment, the pitch direction angle may refer to an angle formed by the first joint member 100 and the second joint member 200 when the first joint member 100 rotates about the first virtual line $IL_1$ in a z-axis direction shown in FIG. 14.

In other words, since the tension of the fifth or sixth sub-string 450 or 460 is smaller than the tension of each of the first to fourth main strings 310, 320, 330, and 340, the artificial joint according to the fourth embodiment may perform the yaw rotation $Y_R$ as well as the pitch rotation $P_R$ unlike the artificial joint according to the second embodiment described with reference to FIG. 6.

Referring to FIG. 15, the artificial joint according to the fourth embodiment may have flexibility $X_F$ in the roll direction Rr and the long-axis direction of the first bone frame 110 and the second bone frame 210 when the pitch direction angle of the first joint member 100 with respect to the second joint member 200 is smaller than the predetermined reference. In addition, the artificial joint according to the fourth embodiment may have flexibility with respect to the force pushing or pulling in the translational Z-axis direction and the translational Y-axis direction.

For the case where the pitch direction angle is smaller than the predetermined reference, the artificial joint according to the fourth embodiment described with reference to FIGS. 14 and 15 may be operated in the same way as a case of the artificial joint according to the third embodiment described with reference to FIGS. 9 and 10 when the pitch direction angle is smaller than the predetermined reference, and may have the same number of flexibility as the above case.

However, in the artificial joint according to the fourth embodiment, when the pitch direction angle of the first joint member 100 with respect to the second joint member 200 is larger than the reference, the degrees of freedom may vary according to the pitch direction as well as the pitch direction angle. Hereinafter, a case in which a pitch direction rotation angle is larger than the reference and a pitch rotation direction is the counterclockwise direction will be described with reference to FIGS. 16 and 17, and a case in which the pitch direction rotation angle is larger than the reference and the pitch rotation direction is the clockwise direction will be described with reference to FIGS. 18 and 19.

FIG. 16 is a view showing a movement of the artificial joint according to the fourth embodiment of the present invention when the pitch direction angle of the artificial joint is larger than the reference and a pitch rotation direction is a counterclockwise direction, and FIG. 17 is a view showing flexibility of the artificial joint according to the fourth embodiment of the present invention when the pitch direction angle of the artificial joint is larger than the reference and the pitch rotation direction is the counterclockwise direction.

Referring to FIG. 16, the artificial joint according to the fourth embodiment may have one rotational degree of freedom for the pitch rotation $P_R$ when the pitch direction angle of the first joint member 100 with respect to the second joint member 200 is larger than the predetermined reference and the pitch direction is the counterclockwise direction (e.g., 90 degrees). In this case, while the first joint member 100 may perform the pitch rotation with respect to the second joint member 200, the tensions of the fifth and sixth sub-strings 450 and 460 may become larger than the predetermined reference. Accordingly, the rotation in the yaw direction is limited.

According to one embodiment, when the pitch direction is referred to as a counterclockwise direction, it may signify that the first joint member 100 rotates with respect to the second joint member 200 about the first virtual line $IL_1$, which is arranged in the Y-axis direction shown in FIG. 16, in the counterclockwise direction.

In detail, as the pitch direction angle of the first joint member 100 with respect to the second joint member 200 increases in the counterclockwise direction, the tensions of the fifth and sixth sub-strings 450 and 460 may be increased. In particular, the tensions of the fifth and sixth sub-strings 450 and 460 may be increased when the pitch direction angle is larger than the predetermined reference and the pitch direction is the counterclockwise direction.

Accordingly, in the artificial joint according to the fourth embodiment, the yaw rotation $Y_R$ of the first joint member 100 with respect to the second joint member 200 may be limited, while the pitch rotation $P_R$ of the first joint member 100 with respect to the second joint member 200 may be performed.

Referring to FIG. 17, the artificial joint according to the fourth embodiment may have the flexibility $X_F$ in the yaw direction $Y_R$, the roll direction Rr, and the long-axis direction of the second bone frame 210 based on the longitudinal direction of the first joint member 100 when the pitch direction angle of the first joint member 100 with respect to the second joint member 200 is larger than the predetermined reference and the pitch direction is the counterclockwise direction.

FIG. 18 is a view showing a movement of the artificial joint according to the fourth embodiment of the present invention when the pitch direction angle of the artificial joint is larger than the reference and the pitch direction is a clockwise direction, and FIG. 19 is a view showing flexibility of the artificial joint according to the fourth embodiment of the present invention when the pitch direction angle of the artificial joint is larger than the reference and the pitch direction is the clockwise direction.

Referring to FIG. 18, the artificial joint according to the fourth embodiment may have two rotational degrees of freedom for the pitch rotation $P_R$ and the yaw rotation $Y_R$ when the pitch direction rotation angle of the first joint member 100 with respect to the second joint member 200 is larger than the predetermined reference and the pitch rotation direction is the clockwise direction. According to one embodiment, when the pitch direction is referred to as a clockwise direction, it may signify that the first joint member 100 rotates with respect to the second joint member 200 about the first virtual line $IL_1$, which is arranged in the Y-axis direction shown in FIG. 18, in the clockwise direction.

In detail, as the pitch direction angle of the first joint member 100 with respect to the second joint member 200 increases in the clockwise direction, the tensions of the fifth and sixth sub-strings 450 and 460 may still remain loose.

Accordingly, in the artificial joint according to the fourth embodiment, as described with reference to FIG. 14, the first joint member 100 may have two rotational degrees of freedom for the pitch rotation $P_R$ and the yaw rotation $Y_R$ with respect to the second joint member 200.

Referring to FIG. 19, the artificial joint according to the fourth embodiment may have the flexibility in the roll direction Rr and the long-axis direction $X_F$ of the second bone frame 210 based on the longitudinal direction of the first joint member 100 when the pitch direction rotation angle of the first joint member 100 with respect to the second joint member 200 is larger than the predetermined reference and the pitch rotation direction is the clockwise direction. As described above, the artificial joint according to the fourth embodiment may also have the flexibility in the translational Z-axis direction and the translational Y-axis direction.

As described above, the artificial joint according to the fourth embodiment of the present invention may provide the rotational degrees of freedom in the pitch direction and the yaw direction when the pitch direction angle is smaller than the reference, and the artificial joint may have the flexibility in other directions due to the flexibility of the main strings. In addition, the artificial joint according to the fourth embodiment of the present invention may provide the rotational degree of freedom in the pitch direction when the pitch direction angle is larger than the reference and the pitch direction is the counterclockwise direction, that is, when the rotation is performed in a direction of a branch that is not connected to a sub-string. Further, the artificial joint according to the fourth embodiment of the present invention may provide the rotational degrees of freedom in the pitch direction and the yaw direction when the pitch direction angle is larger than the reference and the pitch direction is the clockwise direction, that is, when the rotation is performed in a direction of a branch that is connected to a sub-string, and the artificial joint may have the flexibility in other directions due to the flexibility of the main strings.

Accordingly, the artificial joints according to the third and fourth embodiments in which the number of rotational degrees of freedom varies according to the angle between the first joint member 100 and the second joint member 200 have been described. Hereinafter, the artificial joint according to the fifth embodiment having a degree of freedom in pitch in a diagonal direction will be described with reference to FIGS. 20 to 23.

Artificial Joint According to Fifth Embodiment

FIG. 20 is a view showing an artificial joint according to a fifth embodiment of the present invention, FIG. 21 is a perspective view showing a movement of the artificial joint according to the fifth embodiment of the present invention, FIG. 22 is a front view showing the movement of the artificial joint according to the fifth embodiment of the present invention, and FIG. 23 is a view showing flexibility of the artificial joint according to the fifth embodiment of the present invention.

Referring to FIG. 20, compared to the artificial joint according to the first embodiment described with reference to FIG. 1, the artificial joint according to the fifth embodiment may further include at least one of seventh and eighth sub-strings 470 and 480. Accordingly, the detailed descriptions of the first joint member 100, the second joint member 200, and the first to fourth main strings 310, 320, 330, and 340 will be omitted.

According to one embodiment, the seventh sub-string 470 may connect the middle portion of the first-first branch 120 to the middle portion of the second-second branch 230. According to one embodiment, the eighth sub-string 480 may connect a middle portion of the first-second branch 130 to the middle portion of the second-first branch 220.

Referring to FIGS. 21 and 22, in the artificial joint according to the fifth embodiment, the first joint member 100 may have one rotational degree of freedom for the pitch rotation $P_R$ with respect to the second joint member 200. In this case, the artificial joint according to the fifth embodiment includes the seventh and eighth sub-strings 470 and 480, so that the rotational degree of freedom for the pitch rotation $P_R$ may be provided in a diagonal direction when viewed in an X-axis. Accordingly, the artificial joint according to the fifth embodiment may provide a wider movement as compared with the case where the rotational degree of freedom for the pitch rotation $P_R$ is provided in a linear direction. In another point of view, the artificial joint according to the fifth embodiment may provide a movement similar to a movement of an elbow of a human body.

Referring to FIG. 23, in the artificial joint according to the fifth embodiment, the first joint member 100 may have flexibility with respect to the second joint member 200 in the yaw direction $Y_R$, the roll direction Rr, and the long-axis direction $X_F$ of the first bone frame and the second bone frame.

According to the embodiment of the present invention, the artificial joint includes: a first joint member 100 including a first bone frame 110, and a first-first branch 120 and a first-second branch 120 branched to both sides from the first bone frame 110; a second joint member 200 including a second bone frame 210, and a second-first branch 220 and a second-second branch 230 branched to both sides from the second bone frame 210; a first main string 310 configured to connect one side of the first-first branch 120 to one side of the second-first branch 220; a second main string 320 configured to connect the one side of the first-first branch 120 to one side of the second-second branch 230; a third main string 330 configured to connect one side of the first-second branch 130 to the one side of the second-first branch 220; and a fourth main string 340 configured to connect the one side of the first-second branch 130 to the one side of the second-second branch 230. Accordingly, friction between members can be reduced so as to provide an artificial joint that can be used for a long time without abrasion.

In addition, according to the embodiment of the present invention, the artificial joint may further include: first and third sub-strings 410 and 430 configured to connect one side of the first bone frame 110 to the one side of the second-first branch 220; second and fourth sub-strings 420 and 440 configured to connect the one side of the first bone frame to the one side of the second-second branch 230; a fifth sub-string 450 configured to connect the one side of the first-first branch 120 to a middle portion of the second-first branch 220; a sixth sub-string 460 configured to connect the one side of the first-first branch 120 to a middle portion of the second-second branch 230; a seventh sub-string 470 configured to connect a middle portion of the first-first branch 120 to a middle portion of the second-second branch 230; and an eight sub-string 480 configured to connect a middle portion of the first-second branch 130 to a middle portion of the second-first branch 220, wherein a tension of each of the third to sixth sub-strings 430, 440, 450, 460, and 470 may be smaller than a tension of at least one of the first to fourth main strings 310, 320, 330, and 340. Accordingly, an artificial joint capable of generating various rotary joints can be provided.

Further, the artificial joint according to the embodiments of the present invention may be utilized in a human joint, a robot joint, and the like. In other words, the artificial joint may be utilized as a joint mechanism.

Although the exemplary embodiments of the present invention have been described in detail as described above, the scope of the present invention is not limited to a specific embodiment, and should be interpreted by the appended claims. Further, it should be understood by those skilled in the art to which the invention pertains that various changes and modifications can be made without departing from the scope of the present invention.

INDUSTRIAL APPLICABILITY

The artificial joint according to the embodiment of the present invention may be applied to fields associated with robots, rehabilitation devices, and the like in which a rotary joint that requires flexibility is used.

The invention claimed is:

1. An artificial joint comprising:
a first joint member including a first bone frame, and a first-first branch and a first-second branch branched to both sides from the first bone frame;
a second joint member including a second bone frame, and a second-first branch and a second-second branch branched to both sides from the second bone frame;
a first main string configured to connect one side of the first-first branch to one side of the second-first branch;
a second main string configured to connect the one side of the first-first branch to one side of the second-second branch;
a third main string configured to connect one side of the first-second branch to the one side of the second-first branch; and
a fourth main string configured to connect the one side of the first-second branch to the one side of the second-second branch.

2. The artificial joint of claim 1, wherein the first main string and the fourth main string are parallel to each other, and
the second main string and the third main string are parallel to each other.

3. The artificial joint of claim 2, wherein the first joint member has two rotational degrees of freedom with respect to the second joint member.

4. The artificial joint of claim 3, wherein the first joint member is able to perform pitch rotation with respect to the second joint member when viewing the second joint member in a longitudinal direction.

5. The artificial joint of claim 3, wherein the first joint member is able to perform yaw rotation with respect to the second joint member when viewing the second joint member in a longitudinal direction.

6. The artificial joint of claim 2, further comprising:
a first sub-string configured to connect one side of the first bone frame to the one side of the second-first branch; and
a second sub-string configured to connect the one side of the first bone frame to the one side of the second-second branch.

7. The artificial joint of claim 6, wherein the first joint member has one rotational degree of freedom with respect to the second joint member.

8. The artificial joint of claim 7, wherein the first joint member is able to perform pitch rotation with respect to the second joint member when viewing the second joint member in a longitudinal direction.

9. The artificial joint of claim 7, wherein the artificial joint has flexibility in at least one of a yaw direction, a roll direction, and a long-axis direction of the first bone frame and the second bone frame when viewing the second joint member in a longitudinal direction.

10. The artificial joint of claim 2, further comprising:
a third sub-string configured to connect one side of the first bone frame to the one side of the second-first branch; and
a fourth sub-string configured to connect the one side of the first bone frame to the one side of the second-second branch,
wherein a tension of the third or fourth sub-string is smaller than a tension of at least one of the first to fourth main strings.

11. The artificial joint of claim 10, wherein the artificial joint has a different number of rotational degrees of freedom according to a pitch direction angle between the first joint member and the second joint member when viewing the second joint member in a longitudinal direction.

12. The artificial joint of claim 11, wherein the first joint member has two degrees of freedom for pitch rotation and yaw rotation with respect to the second joint member when the pitch direction angle is smaller than a predetermined reference.

13. The artificial joint of claim 12, wherein the first joint member has flexibility with respect to the second joint member in a roll direction and a long-axis direction of the first bone frame and the second bone frame.

14. The artificial joint of claim 11, wherein the first joint member has one degree of freedom for pitch rotation with respect to the second joint member when the pitch direction angle is larger than a predetermined reference.

15. The artificial joint of claim 14, wherein the first joint member has flexibility with respect to the second joint member in a yaw direction, a roll direction, and a long-axis direction of the second bone frame when viewing the second joint member in the longitudinal direction.

16. The artificial joint of claim 2, further comprising:
a fifth sub-string configured to connect the one side of the first-first branch to a middle portion of the second-first branch; and
a sixth sub-string configured to connect the one side of the first-first branch to a middle portion of the second-second branch,
wherein a tension of the fifth or sixth sub-string is smaller than a tension of at least one of the first to fourth main strings.

17. The artificial joint of claim 16, wherein a rotational degree of freedom is reduced in a case where the first joint member performs pitch rotation more than a predetermined reference with respect to the second joint member in a direction of the first-second branch when viewing the second joint member in a longitudinal direction.

18. The artificial joint of claim 2, further comprising:
a seventh sub-string configured to connect a middle portion of the first-first branch to a middle portion of the second-second branch; and
an eight sub-string configured to connect a middle portion of the first-second branch to a middle portion of the second-first branch,
wherein the artificial joint has a degree of freedom in pitch in a diagonal direction.

19. The artificial joint of claim 1, further comprising a sub-string,
wherein the sub-string provides a rotational characteristic between the first joint member and the second joint member.

20. The artificial joint of claim 1, wherein the artificial joint has flexibility in at least one of a roll direction and a long-axis direction of the first bone frame and the second bone frame when viewing the second joint member in a longitudinal direction.

21. The artificial joint of claim 1, wherein a first virtual line configured to connect one end of the second-first branch to one end of the second-second branch and a second virtual line configured to connect one end of the first-first branch to one end of the first-second branch cross each other.

22. The artificial joint of claim 1, wherein in a case where the first joint member rotates with respect to the second joint member in a pitch direction when viewing the second joint member in a longitudinal direction, the first-first branch or the first-second branch passes through a virtual surface defined by a space between the second-first branch and the second-second branch.

\* \* \* \* \*